United States Patent [19]

Haga et al.

[11] Patent Number: 5,229,403

[45] Date of Patent: Jul. 20, 1993

[54] DIAMINOTRIFLUOROMETHYLPYRIDINE DERIVATIVES AND PHOSPHOLIPASE $A_2$ INHIBITOR CONTAINING THEM

[75] Inventors: Takahiro Haga; Hideo Sugi; Itaru Shigehara; Shinji Odawara; Syuichi Yotsuya; Hirohiko Kimura; Kazuhiro Yamamoto, all of Kusatsu, Japan

[73] Assignee: Ishihara Sangyo Kaisha Ltd., Osaka, Japan

[21] Appl. No.: 723,377

[22] Filed: Jun. 28, 1991

[30] Foreign Application Priority Data

Jul. 10, 1990 [JP] Japan .................. 2-181999

[51] Int. Cl.$^5$ ............... A61K 31/44; C07D 213/75
[52] U.S. Cl. ............... 514/352; 514/353; 544/131; 544/316; 544/355; 544/405; 546/112; 546/146; 546/172; 546/192; 546/193; 546/194; 546/261; 546/262; 546/268; 546/285; 546/305; 546/306; 546/307; 546/308; 546/311
[58] Field of Search ............... 546/285, 308, 268, 305, 546/306; 514/352, 353

[56] References Cited

U.S. PATENT DOCUMENTS

| | | | |
|---|---|---|---|
| 3,746,531 | 7/1973 | Doherty | 71/94 |
| 3,961,063 | 6/1976 | Parish | 424/263 |
| 3,962,263 | 6/1976 | Doherty | 71/94 |
| 3,963,660 | 6/1976 | Hall et al. | 546/305 |
| 4,000,285 | 12/1976 | Parish | 424/263 |
| 4,002,761 | 1/1977 | Parish | 424/263 |

FOREIGN PATENT DOCUMENTS 1445677 12/1968 Fed. Rep. of Germany .
2205194 8/1972 Fed. Rep. of Germany .

OTHER PUBLICATIONS

Chemical Abstracts, vol. 100, No. 19, May 7, 1984, p. 526, 156508R, & JP-A-58-198469, Nov. 18, 1983, "Pyridyl-Hydrazide Compounds".

*Primary Examiner*—C. Warren Ivy
*Assistant Examiner*—James H. Turnipseed

*Attorney, Agent, or Firm*—Oblon, Spivak, McClelland, Maier & Neustadt

[57] ABSTRACT

A diaminotrifluoromethylpyridine derivative of the formula (I) or its salt:

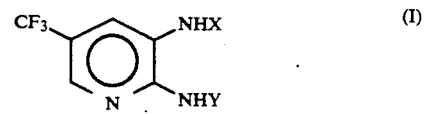

wherein X is $-CW^1R^1$, $-COCOR^2$, $-CW^1NHCOR^2$, $-C(=W^1)(W^2W^3)$ or $-CW^1N(R^4)R^5$, and Y is alkyl, $-CW^3R^6$, $-COCOR^7$, $-NHCOR^7$, $-C(=W^3)W^4R^8$, $-(NH)_mSO_2R^9$, $-(NH)_mSO_2OR^{10}$ or $-(NH)_mSO_2NR^{11})R^{12}$, wherein each of $R^1$, $R^6$ and $R^9$, which are independent from one another, is a chain hydrocarbon group which may be substituted, a monocyclic hydrocarbon group which may be substituted, a polycyclic hydrocarbon group which may be substituted, a monocyclic heterocycle group which may be substituted or a polycyclic heterocycle group which may be substituted, each of $R^2$ and $R^7$, which are independent from each other, is alkyl which may be substituted, alkoxy which may be substituted, phenyl which may be substituted or phenoxy which may be substituted, each of $R^3$, $R^8$ and $R^{10}$, which are independent from one another, is alkyl which may be substituted, alkenyl which may be substituted, alkynyl which may be substituted, cycloalkyl which may be substituted, phenyl which may be substituted or benzyl which may be substituted, each of $R^4$, $R^5$, $R^{11}$ and $R^{12}$, which are independent from one another, is alkyl which may be substituted, each of $W^1$, $W^2$, $W^3$ and $W^4$, which are independent from one another, is an oxygen atom or a sulfur atom, and m is 0 or 1, provided that a combination wherein one of X and Y is $-COCF_2X^1$ wherein $X^1$ is a hydrogen atom, a halogen atom, alkyl or haloalkyl, and the other is $-COCF_2X^2$ wherein $X_2$ is a hydrogen atom, a halogen atom, alkyl, haloalkyl or alkylcarbonyl, or $-COOX^3$ wherein $X^3$ is alkyl which may be substituted or phenyl which may be substituted, is excluded.

5 Claims, No Drawings

DIAMINOTRIFLUOROMETHYLPYRIDINE DERIVATIVES AND PHOSPHOLIPASE $A_2$ INHIBITOR CONTAINING THEM

The present invention relates to novel diaminotrifluoromethylpyridine derivatives or their salts, a process for their production, a phospholipase $A_2$ inhibitor, an anti-inflammatory agent and an anti-pancreatitis agent containing them, and novel trifluoromethylpyridine derivatives as intermediates.

As a diaminotrifluoromethylpyridine derivative, for example, U.S. Pat. Nos. 3,746,531 and 3,962,263 disclose a pyridine as an active ingredient of a herbicide, which has trifluoromethyl at the 5-position, —NHCO—$CF_2$—$T^1$ wherein $T^1$ is a hydrogen atom, a chlorine atom, a fluorine atom, alkyl or haloalkyl at either the 2-position or the 3-position, and —NHCO—$CF_2$-$T^2$ wherein $T^2$ is a hydrogen atom, a chlorine atom, a fluorine atom, alkyl, haloalkyl or alkylcarbonyl, or —NHCOO$T^3$ wherein $T^3$ is $C_{1-4}$ lower alkyl or phenyl at the other position. However, this is different in the chemical structure from the diaminotrifluoromethylpyridine derivative of the present invention. Further, U.S. Pat. No. 3,961,063 discloses a trifluoromethyl-substituted pyridine as an active ingredient of an anthelmintic, which has —NHCSNHCO$T^4$ wherein $T^4$ is alkoxy, at the 2- and 3-positions. However, this compound is different in the chemical structure from the diaminotrifluoromethylpyridine derivative of the present invention.

The present invention provides a diaminotrifluoromethylpyridine derivative of the formula (I) or its salt:

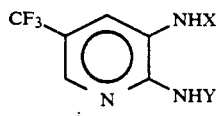
(I)

wherein X is —$CW^1R^1$, —$COCOR^2$, —$CW^1NHCOR^2$, —$C(=W^1)W^2R^3$ or —$CW^1N(R^4)R^5$, and Y is alkyl, —$CW^3R^6$, —$COCOR^7$, —$NHCOR^7$, —$C(=W^3)W^4R^8$, —$(NH)_mSO_2R^9$, —$(NH)_mSO_2OR^{10}$ or —$(NH)_mSO_2N(R^{11})R^{12}$, wherein each of $R^1$, $R^6$ and $R^9$, which are independent from one another, is a chain hydrocarbon group which may be substituted, a monocyclic hydrocarbon group which may be substituted, a polycyclic hydrocarbon group which may be substituted, a monocyclic heterocycle group which may be substituted or a polycyclic heterocycle group which may be substituted, each of $R^2$ and $R^7$, which are independent from each other, is alkyl which may be substituted, alkoxy which may be substituted, phenyl which may be substituted or phenoxy which may be substituted, each of $R^3$, $R^8$ and $R^{10}$, which are independent from one another, is alkyl which may be substituted, alkenyl which may be substituted, alkynyl which may be substituted, cycloalkyl which may be substituted, phenyl which may be substituted or benzyl which may be substituted, each of $R^4$, $R^5$, $R^{11}$ and $R^{12}$, which are independent from one another, is alkyl which may be substituted, each of $W^1$, $W^2$, $W^3$ and $W^4$, which are independent from one another, is an oxygen atom or a sulfur atom, and m is 0 or 1, provided that a combination wherein one of X and Y is —$COCF_2X^1$ wherein $X^1$ is a hydrogen atom, a halogen atom, alkyl or haloalkyl, and the other is —$COCF_2X^2$ wherein $X^2$ is a hydrogen atom, a halogen atom, alkyl, haloalkyl or alkylcarbonyl, or —$COOX^3$ wherein $X^3$ is alkyl which may be substituted or phenyl which may be substituted, is excluded; a process for its production; a phospholipase $A_2$ inhibitor, an anti-inflammatory agent and an anti-pancreatitis agent containing it, and a trifluoromethylpyridine derivative as an intermediate.

Now, the present invention will be described in detail with reference to the preferred embodiments.

In the formula (I), the chain hydrocarbon group for each of $R^1$, $R^6$ and $R^9$ may be alkyl, alkenyl or alkynyl. The monocyclic hydrocarbon group may be cycloalkyl, cycloalkenyl or phenyl. The polycyclic hydrocarbon group may be a condensed polycyclic hydrocarbon group such as naphthyl, tetrahydronaphthyl or indanyl, or a bridged polycyclic hydrocarbon group such as adamantyl, noradamantyl, norbornanyl or norbornanonyl. The monocyclic heterocycle group may be pyrrolyl, furanyl, thienyl, pyrazolyl, imidazolyl, oxazolyl, isoxazolyl, thiazolyl, isothiazolyl, thiadiazolyl, pyrrolinyl, pyrrolidinyl, dihydrofuranyl, tetrahydrofuranyl, dihydrothienyl, tetrahydrothienyl, pyrazolinyl, hydantoinyl, oxazolinyl, isoxazolinyl, isoxazolidinyl, thiazolinyl, thiazolidinyl, dioxolanyl, dithiolanyl, pyridyl, pyridazinyl, pyrimidinyl, pyrazinyl, dihydropyridyl, tetrahydropyridyl, piperidinyl, dihydrooxopyridazinyl, tetrahydrooxopyridazinyl, dihydrooxopyrimidinyl, tetrahydrooxopyrimidinyl, piperazinyl, dihydropyranyl, tetrahydropyranyl, dioxanyl, dihydrodithinyl, dithianyl or morphorinyl. The polycyclic heterocycle group may be a condensed polycyclic heterocycle group such as thienothienyl, dihydrocyclopentathienyl, indolyl, benzofuranyl, benzothienyl, benzoxazolyl, benzisoxazolyl, benzothiazolyl, benzimidazolyl, tetrahydrobenzothienyl, dihydrobenzofuranyl, tetrahydrobenzisoxazolyl, benzodioxolyl, quinolinyl, isoquinolinyl, benzodioxanyl or quinoxalinyl, or a bridged polycyclic heterocycle group such as quinuclidinyl.

The substituent for each of the chain hydrocarbon group which may be substituted for each of $R^1$, $R^6$ and $R^9$, the alkyl which may be substituted and the alkoxy which may be substituted for each of $R^2$ and $R^7$, the alkyl which may be substituted, the alkenyl which may be substituted and the alkynyl which may be substituted for each of $R^3$, $R^8$ and $R^{10}$, the alkyl which may be substituted for each of $R^4$, $R^5$, $R^{11}$ and $R^{12}$ and the alkyl which may be substituted for $X^3$, may be a halogen atom, alkoxy, haloalkoxy, alkylthio, cycloalkyl, cycloalkoxy, cycloalkenyl, cycloalkenyloxy, alkoxycarbonyl, alkylcarbonyl, alkylcarbonyloxy, aryl, aryloxy, arylthio, amino or alkyl-substituted amino. The number of such substituents or substituents on such substituents may be one or more. When the number is two or more, such substituents may be the same or different.

The substituent for each of the monocyclic hydrocarbon group which may be substituted, the polycyclic hydrocarbon group which may be substituted, the monocyclic heterocycle group which may be substituted and the polycyclic heterocycle group which may be substituted for each of $R^1$, $R^6$ and $R^9$, the phenyl which may be substituted and the phenoxy which may be substituted for each of $R^2$ and $R^7$, the cycloalkyl which may be substituted, the phenyl which may be substituted and the benzyl which may be substituted for each of $R^3$, $R^8$ and $R^{10}$, and the phenyl which may be substituted for $X^3$, may be a halogen atom, alkyl, haloalkyl, alkoxy, haloalkoxy, alkylthio, cycloalkyl, cycloalkoxy, cycloalkenyl, cycloalkenyloxy, alkoxycarbonyl, alkylcarbonyl, alkylcarbonyloxy, aryl, aryloxy, arylthio, amino, alkyl-substituted amino, cyano or nitro. The number of such substituents or substituents for such substituents may be one or more. If the number is two or more, such substituents may be the same or different.

In the formula (I), the alkyl group and the alkyl moiety contained in each of X and Y may be $C_{1-18}$ alkyl such as methyl, ethyl, propyl, butyl, pentyl, hexyl, heptyl, octyl, decyl or nonadecyl, and they include linear or branched aliphatic structural isomers. The alkenyl group and the alkenyl moiety contained in each of X and Y may be $C_{2-18}$ alkenyl such as vinyl, propenyl, butenyl, pentenyl, hexenyl, decenyl or nonadecenyl, and they include linear or branched aliphatic structural isomers. The alkynyl group and the alkynyl moiety contained in each of X and Y may be $C_{2-18}$ alkynyl such as ethynyl, propynyl, butynyl, pentynyl, hexynyl, decynyl or nonadecynyl, and they include linear or branched aliphatic structural isomers. The cycloalkyl group and the cycloalkyl moiety contained in each of X and Y may be $C_{3-8}$ cycloalkyl such as cyclopropyl, cyclobutyl, cyclopentyl, cyclohexyl or cyclooctyl. The cycloalkenyl group and the cycloalkenyl moiety contained in each of X and Y may be $C_{5-8}$ cycloalkenyl such as cyclopentenyl, cyclohexenyl or cyclooctenyl. The halogen atom contained in each of X and Y may be a fluorine atom, a chlorine atom, a bromine atom or an iodine atom. The aryl group and the aryl moiety contained in each of X and Y may be phenyl, thienyl, furanyl, pyridyl, naphthyl, benzothienyl, benzofuranyl or quinolinyl.

Now, preferred embodiments of the compound of the present invention will be described. In the formula (I), it is preferred that X is $-CW^1R^1$ or $-C(=W^1)W^2R^3$, and Y is $-SO_2R^9$. Each of $R^1$ and $R^6$ is preferably alkyl which may be substituted, alkenyl which may be substituted, cycloalkyl which may be substituted, cycloalkenyl which may be substituted, phenyl which may be substituted, tetrahydronaphthyl which may be substituted, indanyl which may be substituted or thienyl which may be substituted, more preferably, alkyl, haloalkyl, alkenyl, haloalkenyl, cycloalkyl, halogen-substituted cycloalkyl, phenyl, halogen-substituted phenyl, alkyl- or haloalkyl-substituted phenyl, or alkoxy- or haloalkoxy-substituted phenyl. Each of $R^2$ and $R^7$ is preferably alkoxy which may be substituted or phenyl which may be substituted, more preferably alkoxy, haloalkoxy, phenyl, or halogen-substituted phenyl. Each of $R^3$, $R^8$ and $R^{10}$ is preferably alkyl which may be substituted, more preferably, alkyl or haloalkyl. Each of $R^4$, $R^5$, $R^{11}$ and $R^{12}$ is preferably alkyl. $R^9$ is preferably alkyl which may be substituted, alkenyl which may be substituted, cycloalkyl which may be substituted, cycloalkenyl which may be substituted or phenyl which may be substituted, more preferably alkyl, haloalkyl, phenyl, halogen-substituted phenyl, alkyl- or haloalkyl-substituted phenyl, or alkoxy- or haloalkoxy-substituted phenyl.

Preferred specific compounds of the present invention include N-(2-ethylsulfonylamino-5-trifluoromethyl-3-pyridyl)cyclohexanecarboxamide, N-(2-methylsulfonylamino-5-trifluoromethyl-3-pyridyl)-5-indanecarboxamide, N-(2-methylsulfonylamino-5-trifluoromethyl-3-pyridyl)acetoxyacetamide, N-(2-methylsulfonylamino-5-trifluoromethyl-3-pyridyl)crotonamide, N-(2-methylsulfonylamino-5-trifluoromethyl-3-pyridyl)-2-thiophenecarboxamide, N-(2-methylsulfonylamino-5-trifluoromethyl-3-pyridyl)-3-trifluoromethylbenzamide, N-(2-ethylsulfonylamino-5-trifluoromethyl-3-pyridyl)-3-fluorobenzamide, N-(2-methylsulfonylamino-5-trifluoromethyl-3-pyridyl)-6-(1,2,3,4-tetrahydronaphthalene)carboxamide, N-(2-ethylsulfonylamino-5-trifluoromethyl-3-pyridyl)-crotonamide, N-(2-methylsulfonylamino-5-trifluoromethyl-3-pyridyl)-3-(2-thienyl)acrylamide, and their salts.

The compound of the formula (I) may form a salt when Y is $-SO_2R^9$ wherein $R^9$ is as defined above. Such a salt may be any pharmaceutically acceptable salt, for example, an alkali metal salt such as a potassium salt or a sodium salt, an alkaline earth metal salt such as a calcium salt, or an organic amine salt such as a triethanol amine salt or a tris(hydroxymethyl)aminomethane salt. Such a salt may have crystal water.

The compounds of the formula (I) and (I-1) can be prepared, for example, by processes represented by the following reactions (A) and (B):

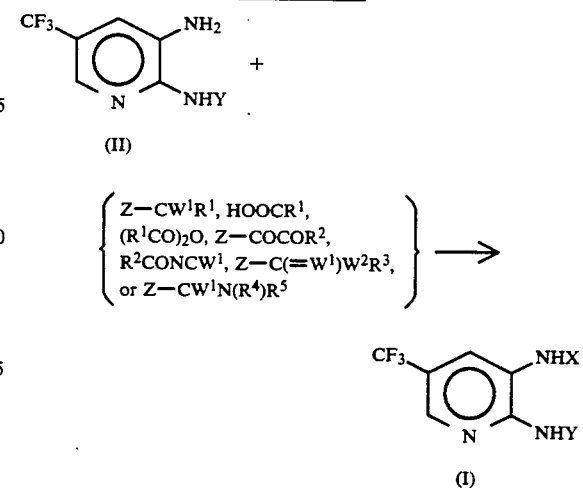

In the above formulas, $R^1$, $R^2$, $R^3$, $R^4$, $R^5$, $W^1$, $W^2$, X and Y are as defined above, and Z is a halogen atom.

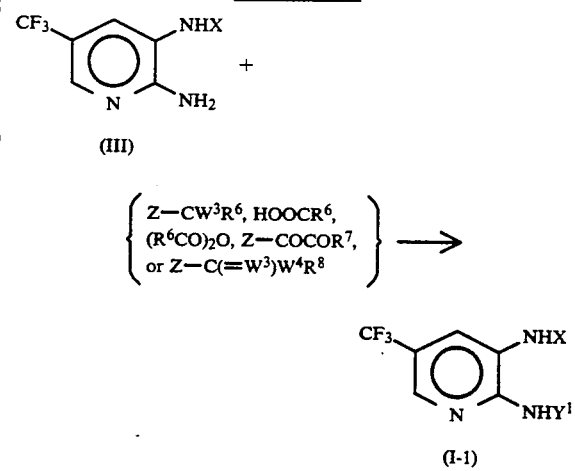

In the above formulas, $Y^1$ is $-CW^3R^6$, $-COCOR^7$ or $-C(=W^3)W^4R^8$, wherein $R^6$, $R^7$, $R^8$, $W^3$, $W^4$, X and Z are as defined above.

A compound of the formula (I-1) wherein X and $Y^1$ are the same substituents, can be prepared in the same manner as the Reaction (B) using as the starting material 2,3-diamino-5-trifluoromethylpyridine instead of the compound of the formula (III).

The reactions (A) and (B) are usually conducted in the presence of a solvent, if necessary, by using a base. The solvent may be an aromatic hydrocarbon such as benzene, toluene, xylene or chlorobenzene; a cyclic or non-cyclic aliphatic hydrocarbon such as chloroform, carbon tetrachloride, methylene chloride, dichloroethane, trichloroethane, n-hexane or cyclohexane; an ether such as diethyl ether, dioxane or tetrahydrofuran; a ketone such as acetone, methyl ethyl ketone or methyl isobutyl ketone; a nitrile such as acetonitrile or propionitrile; an aprotic polar solvent such as dimethylformamide, N-methylpyrrolidone, dimethylsulfoxide or sulfolane. The base may be an inorganic base or an organic base. The inorganic base may, for example, be an alkali metal hydroxide such as sodium hydroxide or potassium hydroxide; an alkali metal or alkaline earth metal carbonate such as anhydrous potassium carbonate or anhydrous calcium carbonate; an alkali metal hydride such as sodium hydride; or an alkali metal such as sodium metal. The organic base may be pyridine or triethylamine.

In the Reactions (A) and (B), a dehydrating condensation agent is required for the reaction with $HOOCR^1$ or $HOOCR^6$. Such a dehydrating condensation agent may be dicyclohexylcarbodiimide, N,N'-carbonyldiimidazole or 1-ethyl-3-(3-dimethylaminopropyl)carbodiimide. The reaction temperature is usually within a range of $-30°$ to $+100°$ C., preferably from $0°$ to $60°$ C., and the reaction time is usually within a range of from 1 to 24 hours, preferably from 1 to 10 hours.

The compound of the formula (II) can be prepared, for example, by processes represented by the following Reactions (C), (D) and (E):

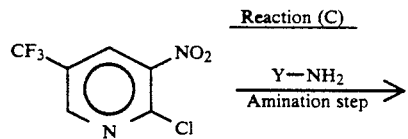

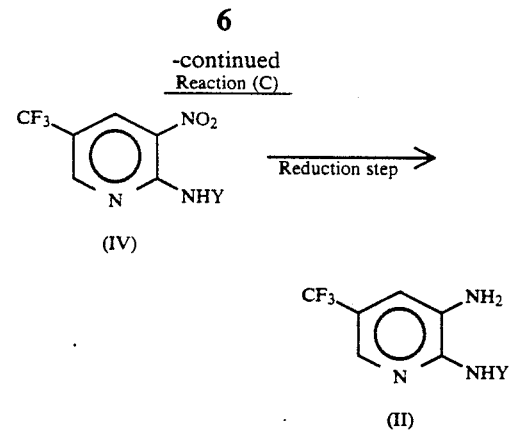

In the above formulas, Y is as defined above.

The amination step in the above Reaction (C) is conducted usually in the presence of a solvent, if necessary, by using a base. The solvent may be an aromatic hydrocarbon such as benzene, toluene, xylene or chlorobenzene; a cyclic or non-cyclic aliphatic hydrocarbon such as chloroform, carbon tetrachloride, methylene chloride, dichloroethane, trichloroethane, n-hexane or cyclohexane; an ether such as diethyl ether, dioxane or tetrahydrofuran; a nitrile such as acetonitrile or propionitrile; or an aprotic polar solvent such as dimethylformamide, N-methylpyrrolidone, dimethylsulfoxide or sulfolane. The base may be the same as the one useful for the above-mentioned Reactions (A) and (B). The reaction temperature is usually within a range of from $-30°$ to $+100°$ C., and the reaction time is usually from 1 to 24 hours.

The reduction reaction in the reduction step in the above Reaction (C) may be conducted by a method wherein an acid such as hydrochloric acid or acetic acid is used together with iron or zinc, a method wherein sodium hydrosulfide, potassium hydrosulfide, sodium sulfide, potassium sulfide or sodium hydrosulfite is used, or a method of catalytic hydrogenation wherein hydrogen is used in the presence of a palladium catalyst or a nickel catalyst. The solvent to be used for the reduction may be optionally selected depending upon the reduction method. Usually, an alcohol such as methanol, ethanol or propanol, water, acetic acid, ethyl acetate, dioxane, tetrahydrofuran or acetonitrile may be employed. The reaction temperature is usually from $0°$ to $100°$ C., and the reaction time is usually from 1 to 24 hours.

(i) In a case where Y is $-CW^3R^6$ or $-COCOR^7$

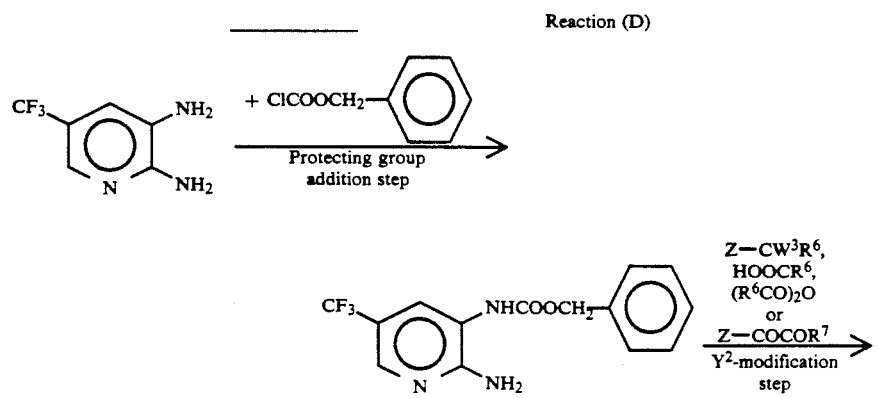

-continued
Reaction (D)

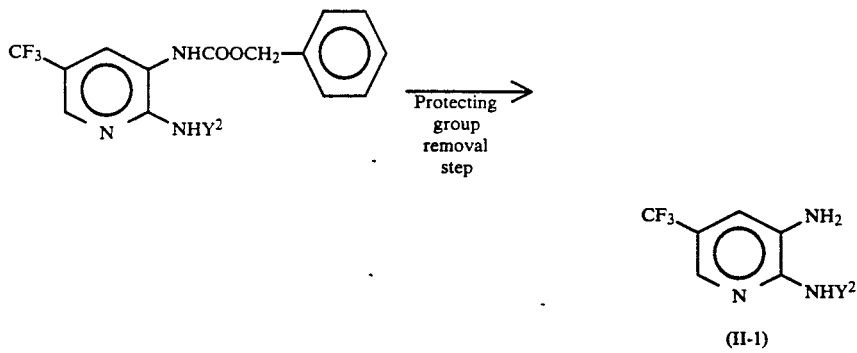

In the above formulas, $Y^2$ is $-CW^3R^6$ or $-COCOR^7$, wherein $R^6$, $R^7$, $W^3$ and $Z$ are as defined above.

The protecting group addition step and the $Y^2$-modification step in the above Reaction (D) can be conducted in the same manner as in the above Reactions (A) and (B). Further, the protecting group removal step in the above Reaction (D) can be conducted by catalytic hydrogenation by means of a palladium catalyst such as palladium carbon usually in the presence of a solvent or by the hydrolysis usually in the presence of a solvent and an acid or base. The solvent may be water; an alcohol such as methanol or ethanol; or an ether such as diethyl ether, dioxane or tetrahydrofuran. The acid may be hydrobromic acid or trifluoroacetic acid. The base may be lithium hydroxide, potassium hydroxide, sodium hydroxide, potassium carbonate or sodium carbonate. The reaction temperature is usually from 0° to 100° C., and the reaction time is usually from 1 to 24 hours.

(ii) In a case where Y is $-SO_2R^{9'}$ ganic base, for example, an alkali metal hydroxide such as sodium hydroxide or potassium hydroxide, or an alkali metal carbonate such as anhydrous potassium carbonate or anhydrous sodium carbonate. The reaction temperature is usually from 80° to 150° C., and the reaction time is usually from 1 to 10 hours.

The sulfonyl-modification step in the above Reaction (E) can be conducted in the same manner as in the above Reactions (A) and (B).

The nitration step in the above Reaction (E) can be conducted by reacting with nitric acid or nitrate usually in the presence of a solvent. The nitrate may be sodium nitrate or potassium nitrate. The solvent may be acetic acid, acetic anhydride or trifluoroacetic acid. The reaction temperature is usually from 50° to 120° C., and the reaction time is usually from 1 to 10 hours.

The reduction step in the above Reaction (E) can be conducted in the same manner as the reduction step in the above Reaction (C).

The compound of the above formula (III) can be

Reaction (E)

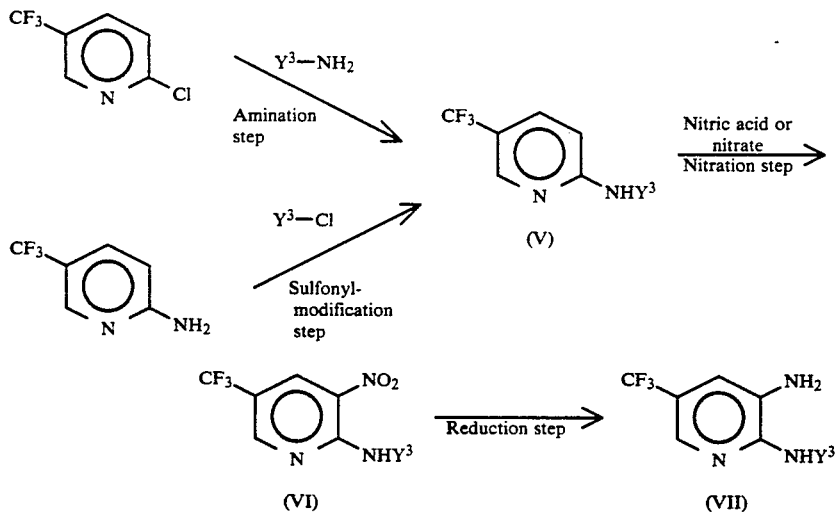

In the above formulas, $Y^3$ is $-SO_2R^{9'}$, $R^{9'}$ is alkyl which may be substituted, alkenyl which may be substituted, cycloalkyl which may be substituted or cycloalkenyl which may be substituted.

The amination step in the above Reaction (E) can be conducted usually in the presence of a solvent by means of a base. The solvent may be an aprotic polar solvent such as dimethyl acetamide, 1,3-dimethyl-2-imidazolidinone or dimethylsulfoxide. The base may be an inorprepared, for example, by a process represented by the following Reaction (F).

Reaction (F)

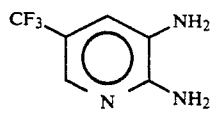
+

$$\left\{\begin{array}{l} Z-CW^1R^1, HOOCR^1, \\ (R^1CO)_2O, Z-COCOR^2, \\ R^2CONCW^1, Z-C(=W^1)W^2R^3, \\ \text{or } Z-CW^1N(R^4)R^5 \end{array}\right\} \longrightarrow$$

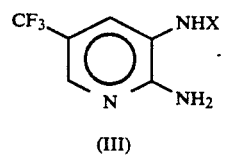

(III)

In the above formulas, $R^1$, $R^2$, $R^3$, $R^4$, $R^5$, $W^1$, $W^2$, $X$ and $Z$ are as defined above.

The above Reaction (F) can be conducted in the same manner as the above Reactions (A) and (B).

Among the compounds of the formula (IV), those wherein Y is $-SO_2R^9$, $-SO_2OR^{10}$ or $-SO_2N(R^{11})R^{12}$, can be produced also by a process represented by the following Reaction (G).

Reaction (G)

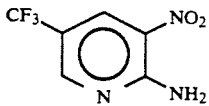
+ $Y^4Cl$ →

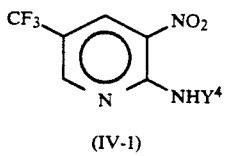

(IV-1)

In the above formulas, $Y^4$ is $-SO_2R^9$, $-SO_2OR^{10}$ or $-SO_2N(R^{11})R^{12}$, wherein $R^9$, $R^{10}$, $R^{11}$ and $R^{12}$ are as defined above.

The above Reaction (G) can be conducted in the same manner as the sulfonyl-modification step in the above Reaction (E).

The compound of the formula (I) can also be prepared by the following alternative method represented by a Reaction (H).

Reaction (H)

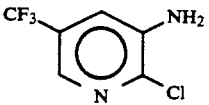
+

$$\left\{\begin{array}{l} Z-CW^1R^1, HOOCR^1, \\ (R^1CO)_2O, Z-COCOR^2, \\ R^2CONCW^1, Z-C(=W^1)W^2R^3, \\ \text{or } Z-CW^1N(R^4)R^5 \end{array}\right\} \xrightarrow{\text{X-modification step}}$$

-continued
Reaction (H)

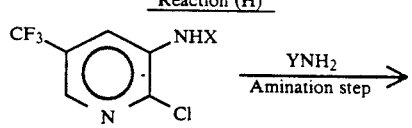

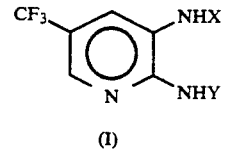

(I)

In the above formulas, $R^1$, $R^2$, $R^3$, $R^4$, $R^5$, $W^1$, $W^2$, $X$, $Y$ and $Z$ are as defined above.

The X-modification step in the above Reaction (H) can be conducted in the same manner as the above Reaction (A), and the amination step is conducted in the same manner as the amination step in the above Reaction (C).

Among the compounds of the above formulas (II), (IV), (IV-1), (V), (VI) and (VII), the following compounds are novel compounds and can be produced by the above Reactions (C), (E) and (G).

Trifluoromethylpyridine derivatives of the formula (VIII):

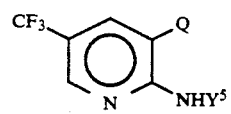

(VIII)

wherein Q is a hydrogen atom, nitro or amino, and $Y^5$ is $-(NH)_m-SO_2R^9$ wherein $R^9$ and m are as defined above, $-(NH)_m-SO_2OR^{10}$ wherein $R^{10}$ and m are as defined above, or $-(NH)_m-SO_2N(R^{11})R^{12}$ wherein $R^{11}$, $R^{12}$ and m are as defined above, provided that when Q is a hydrogen atom and m is 0, $R^9$ is other than naphthyl or phenyl which may be substituted.

Now, Preparation Examples for the compounds of the present invention will be described.

PREPARATION EXAMPLE 1

Preparation of N-(2-ethylsulfonylamino-5-trifluoromethyl-3-pyridyl)-pentafluoropropionamide (Compound No. 19)

(1) 3.1 g of ethanesulfonamide was dissolved in 50 ml of dry tetrahydrofuran, and 1.2 g of 60% sodium hydride was added thereto under cooling with ice. After completion of the addition, the mixture was reacted for one hour under reflux. After cooling, 5.0 g of 2-chloro-3-nitro-5-trifluoromethylpyridine was added thereto, and then the mixture was reacted for 7 hours under reflux. After completion of the reaction, the reaction product was poured into 200 ml of water. Undissolved materials in water were extracted with ethyl ether and removed. Then, the aqueous layer was weakly acidified with dilute hydrochloric acid. Precipitated crystals were collected by filtration and dried to obtain 3.6 g of N-(3-nitro-5-trifluoromethyl-2-pyridyl)ethanesulfonamide having a melting point of from 160° to 163° C.

(2) 1.5 g of N-(3-nitro-5-trifluoromethyl-2-pyridyl)ethanesulfonamide obtained in the above step (1) was dissolved in 30 ml of methanol, and 0.2 g of 5% palladium/carbon was added thereto, and a reduction reaction was conducted under a hydrogen pressure overnight under stirring. After completion of the reaction, 5% palladium/carbon was separated by filtration, and the solvent was distilled off under reduced pressure. The obtained crystals were washed with n-hexane and dried to obtain 1.2 g of N-(3-amino-5-trifluoromethyl-2-pyridyl)ethanesulfonamide having a melting point of from 118° to 120° C.

(3) 0.50 g of N-(3-amino-5-trifluoromethyl-2-pyridyl)ethanesulfonamide obtained in the above step (2) was suspended in 10 ml of dry diethyl ether, and 1.15 g of perfluoropropionic anhydride was dropwise added under cooling with ice. After the dropwise addition, the mixture was stirred for one hour and further reacted at room temperature for one hour. After completion of the reaction, the reaction product was poured into ice water and extracted with ethyl acetate. The extract layer was washed with water and dried, and the solvent was distilled off under reduced pressure. The obtained crystals were washed with n-hexane/ethyl ether to obtain 0.58 g of the desired product (Compound No. 19) having a melting point of from 168° to 170° C.

PREPARATION EXAMPLE 2

Preparation of
N-(2-methylsulfonylamino-5-trifluoromethyl-3-pyridyl)-4-fluorobenzamide (Compound No. 10)

(1) 4.4 g of methanesulfonamide was dissolved in 70 ml of dry tetrahydrofuran, and 1.9 g of 60% sodium hydride was added thereto under cooling with ice. After completion of the addition, the mixture was reacted for one hour under reflux. After cooling, 7.0 g of 2-chloro-3-nitro-5-trifluoromethylpyridine was added thereto, and the mixture was reacted for 6 hours under reflux. After completion of the reaction, the reaction product was poured into 300 ml of water and washed with ethyl ether. Then, the aqueous layer was weakly acidified with dilute hydrochloric acid. Precipitated crystals were collected by filtration and dried to obtain 5.8 g of N-(3-nitro-5-trifluoromethyl-2-pyridyl)methanesulfonamide having a melting point of from 138° to 139° C.

(2) 4.0 g of N-(3-nitro-5-trifluoromethyl-2-pyridyl)methanesulfonamide obtained in the above step (1) was dissolved in 66 ml of methanol, and 0.4 g of 5% palladium/carbon was added thereto. A reduction reaction was conducted under a hydrogen pressure overnight under stirring. After completion of the reaction, 5% palladium/carbon was separated by filtration, and the solvent was distilled off under reduced pressure. The obtained crystals were washed with n-hexane and dried to obtain 3.2 g of N-(3-amino-5-trifluoromethyl-2-pyridyl)methanesulfonamide having a melting point of from 128° to 130° C.

(3) 0.50 g of N-(3-amino-5-trifluoromethyl-2-pyridyl)methanesulfonamide obtained in the above step (2) was dissolved in 6 ml of dry tetrahydrofuran, and 0.37 g of p-fluorobenzoyl chloride was dropwise added under cooling with ice. After the dropwise addition, the mixture was stirred for one hour and further reacted at room temperature overnight. After completion of the reaction, the reaction product was poured into ice water and extracted with ethyl acetate. The extract layer was washed with water and dried. The solvent was distilled off under reduced pressure, and the residue thereby obtained was crystallized from n-hexane/ethyl ether to obtain 0.61 g of the desired product (Compound No. 10) having a melting point of from 211° to 213° C.

PREPARATION EXAMPLE 3

Preparation of
N-(3-trichloroacetylamino-5-trifluoromethyl-2-pyridyl)trifluoroacetamide (Compound No. 30)

(1) Into 38 ml of dry tetrahydrofuran, 1.5 g of 2,3-diamino-5-trifluoromethylpyridine was dissolved, and a solution mixture comprising 1.54 g of trichloroacetyl chloride and 3.8 ml of dry tetrahydrofuran was dropwise added thereto over a period of 10 minutes. Then, the mixture was reacted at room temperature for 3 hours. After completion of the reaction, precipitated crystals were collected by filtration and washed with tetrahydrofuran to obtain 2.2 g of N-(2-amino-5-trifluoromethyl-3-pyridyl)trichloroacetamide having a melting point of from 210° to 223° C.

(2) 2.20 g of N-(2-amino-5-trifluoromethyl-3-pyridyl)trichloroacetamide obtained in the above step (1) was dissolved in 45 ml of dry tetrahydrofuran, and a solvent mixture comprising 2.15 g of trifluoroacetic anhydride and 3 ml of dry tetrahydrofuran was dropwise added thereto under cooing with ice. After the dropwise addition, the mixture was reacted at room temperature for 3 hours. After completion of the reaction, the solvent was distilled off under reduced pressure, and the obtained crystals were washed with ethyl ether to obtain 1.20 g of the desired product (Compound No. 30) having a melting point of from 166° to 168° C.

PREPARATION EXAMPLE 4

Preparation of
N-(2-ethylsulfonylamino-5-trifluoromethyl-3-pyridyl)-cyclohexanecarboxamide (Compound No. 47)

(1) 20.3 g of ethanesulfonamide and 26.0 g of 2-chloro-5-trifluoromethylpyridine were dissolved in 220 ml of dimethylsulfoxide, and 47.4 g of anhydrous potassium carbonate was further added thereto. This solution mixture was heated to 130° C. and reacted for 5 hours. After completion of the reaction, the reaction product was poured into 1 l of water. Undissolved materials in water were extracted with ethyl ether and removed. Then, the aqueous layer was adjusted to pH4 with concentrated hydrochloric acid, and precipitated crystals were collected by filtration and dried to obtain 26.2 g of N-(5-trifluoromethyl-2-pyridyl)ethanesulfonamide having a melting point of from 164° to 165° C.

(2) 45 g of N-(5-trifluoromethyl-2-pyridyl)ethanesulfonamide was dissolved in 112.5 ml of acetic acid. While heating it to a temperature of from 100° to 105° C., 26 g of fuming nitric acid (94%) was dropwise added, and the mixture was reacted for further 6 hours. The reaction product was left to cool to 80° C., and then poured into 2 l of ice water. Precipitated crystals were collected by filtration, washed with water and dried to obtain 47.8 g of N-(3-nitro-5-trifluoromethyl-2-pyridyl)ethanesulfonamide.

(3) 3.0 g of N-(3-nitro-5-trifluoromethyl-2-pyridyl)ethanesulfonamide was suspended in a solvent mixture comprising 30 ml of water and 30 ml of acetic acid, and 2.2 g of reduced iron was added thereto. Then, the mixture was heated to 50° C. and reacted for one hour. After completion of the reaction, the reaction product was cooled to room temperature, and excess iron was separated by filtration. The filtrate was extracted with ethyl acetate. The extract layer was washed with water and dried. Ethyl acetate was distilled off under reduced pressure to obtain 2.5 g of N-(3-amino-5-trifluoromethylethyl-2-pyridyl)ethanesulfonamide.

An alternative process will be described. To a solution prepared by dissolving 34.9 g of sodium hydrosulfite in 400 ml of water, a solution prepared by dissolving 5.0 g of N-(3-nitro-5-trifluoromethyl-2-pyridyl)ethanesulfonamide in 80 ml of tetrahydrofuran, was dropwise added at room temperature. After completion of the dropwise addition, the mixture was reacted for further 3 hours. After completion of the reaction, sodium chloride was added until the tetrahydrofuran layer was separated. The separated tetrahydrofuran layer was dried, and tetrahydrofuran was distilled off under reduced pressure to obtain 4.2 g of N-(3-amino-5-trifluoromethyl-2-pyridyl)ethanesulfonamide.

(4) 2.36 g of N-(3-amino-5-trifluoromethyl-2-pyridyl-)ethanesulfonamide was dissolved in 24 ml of dry tetrahydrofuran, and 1.54 g of cyclohexanecarbonyl chloride was dropwise added thereto under cooing with ice. After the dropwise addition, the mixture was stirred for one hour and further reacted at room temperature overnight. After completion of the reaction, the solvent was distilled off under reduced pressure, the obtained crystals were washed with ethyl ether to obtain 2.94 g of the desired product having a melting point of from 153° to 155° C.

An alternative process will be described. In 20 ml of methylene chloride, 0.5 g of 4-diemthylaminopyridine was dissolved, and 0.78 g of 1-ethyl-3-(3-dimethylaminopropyl)carbodiimide hydrochloride was added and dissolved. Then, 1 g of N-(3-amino-5-trifluoromethyl-2-pyridyl)ethanesulfonamide was added thereto, and 30 minutes later, 0.52 g of cyclohexane-carboxylic acid was added thereto, and stirring was conducted for 10 hours. After completion of the reaction, 40 ml of methylene chloride was added to the reaction product, and the reaction product was washed with 10% hydrochloric acid and then washed with an aqueous sodium chloride solution and then dried over anhydrous sodium sulfate. From the extract layer, solvent was distilled off and the obtained residue was purified by silica gel column chromatography to obtain 0.88 g of the desired product.

PREPARATION EXAMPLE 5

Preparation of sodium salt of N-(2-ethylsulfonylamino-5-trifluoromethyl-3-pyridyl)-cyclohexanecarboxamide (Compound No. 251)

To 10 ml of an ethanol solution containing 1.00 g of N-(2-ethylsulfonylamino-5-trifluoromethyl-3-pyridyl)-cyclohexanecarboxamide, 2.75 g of a 1N-sodium hydroxide aqueous solution was added under stirring at 40° C., and the mixture was stirred for one hour. After completion of the reaction, the solvent was distilled off under reduced pressure, and the obtained crystals were washed with ethyl ether to obtain 1.02 g of the desired product which decomposed at 299° C.

Trifluoromethylpyridine compounds of the above formula (VIII) are listed in Table 1.

TABLE 1

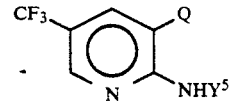

(VIII)

| Intermediate No. | Q | $Y^5$ | Melting point (°C.) |
|---|---|---|---|
| 1 | H | $-SO_2CH_3$ | 189~191 |
| 2 | H | $-SO_2C_2H_5$ | 164~165 |
| 3 | H | $-SO_2CH_2CH_2CH_3$ | 157~159 |
| 4 | H | $-SO_2CH_2CH_2CH_2CH_3$ | 148~150 |
| 5 | H | 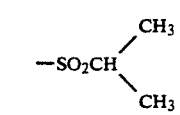 | 181~184 |
| 6 | H | 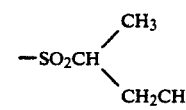 | |
| 7 | H | $-SO_2CH_2CH=CH_2$ | |
| 8 | H | 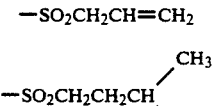 | |
| 9 | H | $-SO_2CH_2C(CH_3)=CH_2$ | |
| 10 | H | $-SO_2CH_2CH_2OCH_2CH_3$ | |
| 11 | H | $-SO_2CF_3$ | 215~218 |
| 12 | H | 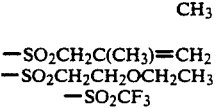 | |
| 13 | H |  | |
| 14 | H | 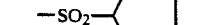 | |
| 15 | H | $-SO_2C_8H_{17}(n)$ | |
| 16 | H | $-SO_2C_{18}H_{37}(n)$ | |
| 17 | H | $-SO_2CF_2CF_3$ | |
| 18 | $NO_2$ | $-SO_2CH_3$ | 138~139 |
| 19 | $NO_2$ | $-SO_2CH_2CH_3$ | 160~163 |
| 20 | $NO_2$ | 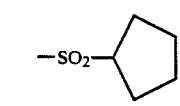 | 138~140 |
| 21 | $NO_2$ | $-SO_2CH_2CH_2CH_3$ | 109~112 |
| 22 | $NO_2$ | $-SO_2CH_2CH_2CH_2CH_3$ | 76~78 |
| 23 | $NO_2$ | 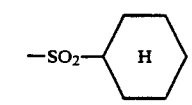 | 138~140 |
| 24 | $NO_2$ | 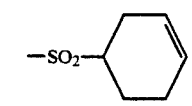 | 145~146 |
| 25 | $NO_2$ | $-NHSO_2CH_3$ | 175~182 |

TABLE 1-continued structure (VIII): 5-CF₃ pyridine with Q at 3-position and NHY⁵ at 2-position

| Intermediate No. | Q | Y⁵ | Melting point (°C.) |
|---|---|---|---|
| 26 | NO₂ | —NHSO₂—C₆H₅ | |
| 27 | NO₂ | —SO₂—C₆H₅ | |
| 28 | NO₂ | —NHSO₂N(CH₃)₂ | |
| 29 | NO₂ | —SO₂CH₂C(CH₃)=CH₂ | 51~56 |
| 30 | NO₂ | —SO₂-cyclohexyl | 156~158 |
| 31 | NO₂ | —SO₂-(2-naphthyl) | |
| 32 | NO₂ | —SO₂-(indanyl) | |
| 33 | NO₂ | —SO₂-(2-furyl) | |
| 34 | NO₂ | —SO₂-(4-COOC₂H₅-1-methylpyrazol-5-yl) | 130~132 |
| 35 | NO₂ | —SO₂-(1-methylimidazol-5-yl) | |
| 36 | NO₂ | —SO₂-(3,5-dimethylisoxazol-4-yl) | |
| 37 | NO₂ | —SO₂-(3-methyl-5-CF₃CH₂O-isothiazol-4-yl) | 192~194 |
| 38 | NO₂ | —SO₂-pyrrolidinyl | |
| 39 | NO₂ | —SO₂-(2-pyrimidinyl) | |
| 40 | NO₂ | —SO₂-(3-pyridazinyl) | |
| 41 | NO₂ | —SO₂-piperidinyl | |
| 42 | NO₂ | —SO₂-morpholinyl | |
| 43 | NO₂ | —SO₂-(3-methylbenzothiophen-2-yl) | |
| 44 | NO₂ | —SO₂-(benzothiazol-2-yl) | |
| 45 | NO₂ | —SO₂-(quinolin-8-yl) | |
| 46 | NO₂ | —SO₂-(2,3-dihydro-1,4-benzodioxin-6-yl) | |
| 47 | NO₂ | —SO₂CH₂C₆H₅ | |
| 48 | NO₂ | —SO₂N(CH₃)₂ | 148~149 |

TABLE 1-continued (VIII) Structure: CF$_3$ on pyridine with Q and NHY$^5$ substituents

| Intermediate No. | Q | Y$^5$ | Melting point (°C.) |
|---|---|---|---|
| 49 | NO$_2$ | —SO$_2$—C$_6$H$_4$—OCH$_3$ | 132 |
| 50 | NO$_2$ | —SO$_2$CF$_3$ | 126~127 |
| 51 | NO$_2$ | —SO$_3$CH$_3$ | 93~94 |
| 52 | NO$_2$ | —SO$_3$C$_2$H$_5$ | 120~121 |
| 53 | NO$_2$ | —SO$_2$-(thienyl) | 104~105 |
| 54 | NO$_2$ | —SO$_2$-(pyridyl) | |
| 55 | NH$_2$ | —SO$_2$CH$_3$ | 128~130 |
| 56 | NH$_2$ | —SO$_2$CH$_2$CH$_3$ | 118~120 |
| 57 | NH$_2$ | —SO$_2$CH(CH$_3$)$_2$ | 155~157 |
| 58 | NH$_2$ | —SO$_2$CH$_2$CH$_2$CH$_3$ | 82~84 |
| 59 | NH$_2$ | —SO$_2$CH$_2$CH$_2$CH$_2$CH$_3$ | 102~103 |
| 60 | NH$_2$ | —SO$_2$-C$_6$H$_5$ | 200~204 |
| 61 | NH$_2$ | —SO$_2$-C$_6$H$_4$-CH$_3$ | 170~175 |
| 62 | NH$_2$ | —NHSO$_2$CH$_3$ | 128~133 |
| 63 | NH$_2$ | —NHSO$_2$O-C$_6$H$_5$ | |
| 64 | NH$_2$ | —SO$_2$O-C$_6$H$_5$ | |
| 65 | NH$_2$ | —NHSO$_2$N(CH$_3$)$_2$ | |
| 66 | NH$_2$ | —SO$_2$CH$_2$C(CH$_3$)=CH$_2$ | 136~139 |
| 67 | NH$_2$ | —SO$_2$-(cyclohexyl) | 164~168 |
| 68 | NH$_2$ | —SO$_2$-(naphthyl) | |
| 69 | NH$_2$ | —SO$_2$-(indanyl) | |
| 70 | NH$_2$ | —SO$_2$-(furyl) | |
| 71 | NH$_2$ | —SO$_2$-(1-methyl-4-ethoxycarbonylpyrazol-5-yl) | 171~174 |
| 72 | NH$_2$ | —SO$_2$-(1-methylimidazol-5-yl) | |
| 73 | NH$_2$ | —SO$_2$-(3,5-dimethylisoxazol-4-yl) | |
| 74 | NH$_2$ | —SO$_2$-(3-methyl-5-trifluoroethoxyisothiazol-4-yl) | 168~173 |
| 75 | NH$_2$ | —SO$_2$-N(pyrrolidinyl) | |
| 76 | NH$_2$ | —SO$_2$-(pyrimidin-2-yl) | |
| 77 | NH$_2$ | —SO$_2$-(pyrazin-2-yl) | |

TABLE 1-continued

Structure (VIII):

CF₃ group at position 5, Q at position 3, NHY⁵ at position 2 of pyridine ring

| Intermediate No. | Q | Y⁵ | Melting point (°C.) |
|---|---|---|---|
| 78 | NH₂ | —SO₂—N(piperidine) | |
| 79 | NH₂ | —SO₂—N(morpholine) | |
| 80 | NH₂ | —SO₂—C(CH₃)=C-benzothiophene | |
| 81 | NH₂ | —SO₂-benzothiazol-2-yl | |
| 82 | NH₂ | —SO₂-quinolin-8-yl | |
| 83 | NH₂ | —SO₂-(1,4-benzodioxin-6-yl) | |
| 84 | NH₂ | —SO₂CH₂-phenyl | |
| 85 | NH₂ | —SO₂N(CH₃)₂ | 165~167 |
| 86 | NH₂ | —SO₂-C₆H₄-OCH₃ | 134~136 |
| 87 | NH₂ | —SO₂CF₃ | 122~124 |
| 88 | NH₂ | —SO₃CH₃ | 97~100 |
| 89 | NH₂ | —SO₃C₂H₅ | 131~132 |
| 90 | NH₂ | —SO₂-thiophen-2-yl | 223~227 |
| 91 | NH₂ | —SO₂-pyridin-2-yl | |

Compounds of the above formula (II) which are not included in the compounds of the above formula (VIII) are listed in Table 2.

TABLE 2

Structure (II): CF₃ at position 5, NH₂ at position 3, NHY at position 2 of pyridine ring

| Intermediate No. | Y | Melting point (°C.) |
|---|---|---|
| 100 | —NHCO-phenyl | 207~210 |
| 101 | —NHCOOCH₂CH₃ | 187~192 |
| 102 | —COOCH₂CH₃ | 289~292 |
| 103 | —NHCOCH₃ | |
| 104 | —COO-phenyl | |
| 105 | —COSCH₂-phenyl | |
| 106 | —CH₃ | |
| 107 | —CH₂CH₃ | |
| 108 | —COCH₃ | |
| 109 | —COCH₂CH=CH₂ | |
| 110 | —CO-phenyl | |
| 111 | —CO-cyclohexyl (H) | |
| 112 | —CO-thiophen-2-yl | |
| 113 | —CO-tetrahydronaphthyl (H) | |
| 114 | —CO-(1,4-benzodioxin-6-yl) | |
| 115 | —CO-pyridin-2-yl | |
| 116 | —COCOCH₃ | |

TABLE 2-continued (II) Structure: CF₃-pyridine with NH₂ and NHY substituents

| Intermediate No. | Y | Melting point (°C.) |
|---|---|---|
| 117 | —COCO—C₆H₅ | |

Compounds of the above formula (III) are listed in Table 3.

TABLE 3

(III) Structure: CF₃-pyridine with NHX and NH₂ substituents

| Intermediate No. | X | Melting point (°C.) |
|---|---|---|
| 118 | —COCHCl₂ | 170~171 |
| 119 | —COCCl₃ | 141~143 |
| 120 | —COOCH₂CH₃ | 151~154 |
| 121 | —COOCH₂—C₆H₅ | 156~158 |
| 122 | —COCOCH₃ | |
| 123 | —COCO—C₆H₅ | |
| 124 | —CONHCOCH₃ | |
| 125 | —CO—C₆H₅ | |
| 126 | —CO—C₆H₁₁ (cyclohexyl) | 248~251 |

Compounds of the above formula (IV) which are not included in the compounds of the above formula (VIII) are listed in Table 4.

TABLE 4

(IV) Structure: CF₃-pyridine with NO₂ and NHY² substituents

| Intermediate No. | Y² | Melting point (°C.) |
|---|---|---|
| 127 | —NHCO—C₆H₅ | 189~195 |
| 128 | —NHCOOCH₂CH₃ | 97~99 |
| 129 | —NHCOCH₃ | |
| 130 | —CH₃ | |
| 131 | —CH₂CH₃ | |

Typical specific examples of the compound of the formula (I) of the present invention are listed in Table 5.

TABLE 5

(I) Structure: CF₃-pyridine with NHX and NHY substituents

| Compound No. | X | Y | Type of salt | Melting point (°C.) |
|---|---|---|---|---|
| 1 | —CO(CH₂)₂CH₃ | —SO₂CH₃ | | 113~114 |
| 2 | —CO(CH₂)₃CH₃ | —SO₂CH₃ | | 119~121 |
| 3 | —CO(CH₂)₄CH₃ | —SO₂CH₃ | | 119~122 |
| 4 | —CO(CH₂)₇CH₃ | —SO₂CH₃ | | 99~101 |
| 5 | —CO(CH₂)₁₀CH₃ | —SO₂CH₃ | | 94~97 |
| 6 | —CO(CH₂)₁₄CH₃ | —SO₂CH₃ | | 99~103 |
| 7 | —COCH₂C(CH₃)₃ | —SO₂CH₃ | | 150~151 |
| 8 | —CO—C₆H₁₁ (cyclohexyl) | —SO₂CH₃ | | 110~116 |
| 9 | —COCH=CH₂ | —SO₂CH₃ | | 174~176 |

TABLE 5-continued (I)

Structure: pyridine with CF₃ at 5-position, NHX at 3-position, NHY at 2-position

| Compound No. | X | Y | Type of salt | Melting point (°C.) |
|---|---|---|---|---|
| 10 | —CO—C₆H₄—F (para) | —SO₂CH₃ | | 211~213 |
| 11 | —COCF₂Cl | —SO₂CH₃ | | 199~201 |
| 12 | —COCF₃ | —SO₂CH₃ | | 154~157 |
| 13 | —COCF₂CF₃ | —SO₂CH₃ | | 186~189 |
| 14 | —COCF₂CF₂CF₃ | —SO₂CH₃ | | 170~173 |
| 15 | —COOC₂H₅ | —SO₂CH₃ | | 180~182 |
| 16 | —COO(CH₂)₂CH₃ | —SO₂CH₃ | | 173-176 |
| 17 | —COO(CH₂)₃CH₃ | —SO₂CH₃ | | 127~129 |
| 18 | —CSNHCOOC₂H₅ | —SO₂CH₃ | | More than 300 |
| 19 | —COCF₂CF₃ | —SO₂C₂H₅ | | 168-170 |
| 20 | —COCF₂Cl | —SO₂C₂H₅ | | 171~174 |
| 21 | —CSNHCOOC₂H₅ | —SO₂C₂H₅ | | More than 300 |
| 22 | —COCF₂CF₃ | —SO₂C₃H₇(n) | | 129~133 |
| 23 | —COCF₂CF₃ | —SO₂C₈H₁₇(n) | | 109~112 |
| 24 | —COCF₃ | —SO₂—C₆H₅ | | 160-163 |
| 25 | —CSNHCOOC₂H₅ | —SO₂—C₆H₄—CH₃ | | 195~200 |
| 26 | —CO(CH₂)₂OC₂H₅ | —CO(CH₂)₂OC₂H₅ | | 75~76 |
| 27 | —COCF₃ | —COCHCl₂ | | 117~119 |
| 28 | —COCHCl₂ | —COCHCl₂ | | 158~159 |
| 29 | —COCHCl₂ | —COCF₃ | | 177~178 |
| 30 | —COCCl₃ | —COCF₃ | | 166~168 |
| 31 | —COO—C₆H₁₁ (cyclohexyl) | —SO₂C₂H₅ | | 135~137 |
| 32 | —CO—C₆H₅ | —COCF₂CF₃ | | 228~230 |
| 33 | —COCH₂—(2-thienyl) | —SO₂C₂H₅ | | 130~134 |
| 34 | —CO—(1,4-benzodioxan-6-yl) | —SO₂CH₃ | | 218~222 |
| 35 | —CO—(2,2-difluoro-1,4-benzodioxan-6-yl) | —SO₂CH₃ | | 219~224 |
| 36 | —CO—(thiazolyl) | —SO₂C₂H₅ | | |

TABLE 5-continued

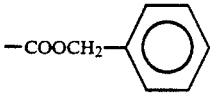
(I)

| Compound No. | X | Y | Type of salt | Melting point (°C.) |
|---|---|---|---|---|
| 37 | —COOC₂H₅ | —COOC₂H₅ | | 112~114 |
| 38 | —COOCH₂—C₆H₅ | —COOC₂H₅ | | 134~137 |
| 39 | —COCF₂CF₃ | —NHCO—C₆H₅ | | 214~217 |
| 40 | —COCF₂CF₃ | —NHSO₂CH₃ | | 136~138 |
| 41 | —COCF₂CF₃ | —CH₃ | | 89~90 |
| 42 | —CO—C₆H₁₁ (cyclohexyl) | —NHCOCH₃ | | |
| 43 | —CO—C₆H₅ | —SO₂CH₃ | | 189~192 |
| 44 | —CO—C₆H₄—OCH₃ | —SO₂CH₃ | | 217~220 |
| 45 | —CO—C₅H₉ (cyclopentyl) | —SO₂CH₃ | | 153–155 |
| 46 | —CO(CH₂)₄Cl | —SO₂CH₃ | | 79~85 |
| 47 | —CO—C₆H₁₁ (cyclohexyl) | —SO₂CH₂CH₃ | | 153~155 |
| 48 | —CO—C₆H₅ | —SO₂CH₂CH₃ | | 204~210 |
| 49 | —COCH=CH₂ | —SO₂CH₂CH₃ | | 148~151 |
| 50 | —COCCl₃ | —SO₂CH(CH₃)₂ | | 178~180 |
| 51 | —COCF₂CF₃ | —SO₂CH(CH₃)₂ | | 161~163 |
| 52 | —COCF₂CF₃ | —SO₂CH₂CH₂CH₂CH₃ | | 146~149 |

TABLE 5-continued (I)

Structure: pyridine with CF3 at 5-position, NHX at 3-position, NHY at 2-position.

| Compound No. | X | Y | Type of salt | Melting point (°C.) |
|---|---|---|---|---|
| 53 | —CO—(cyclohexyl) | —SO₂CH₂CH₂CH₂CH₃ | | 152~154 |
| 54 | —CSNHCOOC₂H₅ | —CH₃ | | 191~193 |
| 55 | —COCH=CHCH₃ | —SO₂CH₃ | | 158~161 |
| 56 | —CO—(4-F-phenyl) | —SO₂C₂H₅ | | 234~237 |
| 57 | —CO—(2-F-phenyl) | —SO₂CH₃ | | 210~214 |
| 58 | —CO—(3-F-phenyl) | —SO₂CH₃ | | 220~222 |
| 59 | —CO—CF₂CF₂H | —SO₂C₂H₅ | | |
| 60 | —COCH₂—(phenyl) | —SO₂CH₃ | | 163~166 |
| 61 | —COCH₂—(2-thienyl) | —SO₂CH₃ | | 172~174 |
| 62 | —COCH₂—(cyclopentyl) | —SO₂CH₃ | | 147~148 |
| 63 | —COCH₂OCOCH₃ | —SO₂CH₃ | | 155~156 |
| 64 | —COCH₂CH₂—(phenyl) | —SO₂CH₃ | | 163~165 |
| 65 | —COCH(C₂H₅)(CH₂)₃CH₃ | —SO₂CH₃ | | 141~144 |
| 66 | —COCH(-phenyl-)CH₂CH₃ | —SO₂CH₃ | | 128~130 |
| 67 | —CO—(cycloheptyl) | —SO₂CH₃ | | 126~130 |

TABLE 5-continued $$\text{(I)} \quad \underset{N}{\underset{\|}{\bigcirc}}\overset{CF_3}{\underset{NHY}{\bigvee}}\overset{NHX}{}$$

| Compound No. | X | Y | Type of salt | Melting point (°C.) |
|---|---|---|---|---|
| 68 | -CO-(cyclohex-3-enyl) | -SO$_2$CH$_3$ | | 143~145 |
| 69 | -CO-(cyclohex-1-enyl) | -SO$_2$CH$_3$ | | 176~179 |
| 70 | -COCH=C(CH$_3$)$_2$ | -SO$_2$CH$_3$ | | 187~188 |
| 71 | -COCH=CH-phenyl | -SO$_2$CH$_3$ | | 215~218 |
| 72 | -COCH=CH-(2-thienyl) | -SO$_2$CH$_3$ | | 227~229 |
| 73 | -COCH=CHCH=CHCH$_3$ | -SO$_2$CH$_3$ | | 300 |
| 74 | -CO(CH$_2$)$_2$CH=CH$_2$ | -SO$_2$CH$_3$ | | 91~93 |
| 75 | -COC≡C-phenyl | -SO$_2$CH$_3$ | | 209~210 |
| 76 | -CO-(2,4-difluorophenyl) | -SO$_2$CH$_3$ | | 245~249 |
| 77 | -CO-(3,4-difluorophenyl) | -SO$_2$CH$_3$ | | 229~231 |
| 78 | -CO-(3-methylphenyl) | -SO$_2$CH$_3$ | | 187~189 |
| 79 | -CO-(3-chlorophenyl) | -SO$_2$CH$_3$ | | 198~201 |
| 80 | -CO-(3-trifluoromethylphenyl) | -SO$_2$CH$_3$ | | 230~233 |

TABLE 5-continued

Structure (I):
5-CF$_3$-pyridine with 3-NHX and 2-NHY substituents

| Compound No. | X | Y | Type of salt | Melting point (°C.) |
|---|---|---|---|---|
| 81 | −CO−(C$_6$H$_4$)−C$_2$H$_5$ | −SO$_2$CH$_3$ | | 211~215 |
| 82 | −CO−(4-pyridyl) | −SO$_2$CH$_3$ | | 206~210 |
| 83 | −CO−(5-methylthien-2-yl) | −SO$_2$CH$_3$ | | 207~210 |
| 84 | −CO−(thien-3-yl) | −SO$_2$CH$_3$ | | 202~205 |
| 85 | −CO−(furan-2-yl) | −SO$_2$CH$_3$ | | 227~231 |
| 86 | −CO−(benzothiophen-2-yl) | −SO$_2$CH$_3$ | | 250~252 |
| 87 | −CO−(indan-5-yl) | −SO$_2$CH$_3$ | | 194~197 |
| 88 | −CO−(4,5,6,7-tetrahydrobenzothiophen-2-yl) | −SO$_2$CH$_3$ | | 229~233 |
| 89 | −COCCl$_2$CH$_3$ | −SO$_2$CH$_3$ | | 212~214 |
| 90 | −COCOC$_6$H$_5$ | −SO$_2$CH$_3$ | | 231~234 |
| 91 | −CO−(cyclohexyl) | −SO$_2$CF$_3$ | | 175~178 |
| 92 | −CO−(thien-2-yl) | −SO$_2$CF$_3$ | | 209~210 |
| 93 | −COCH=CHCH$_3$ | −SO$_2$C$_2$H$_5$ | | 158~160 |
| 94 | −CO−(cyclopentyl) | −SO$_2$C$_2$H$_5$ | | 157~161 |

TABLE 5-continued (I)

structure: pyridine with CF₃, NHX, NHY substituents

| Compound No. | X | Y | Type of salt | Melting point (°C.) |
|---|---|---|---|---|
| 95 | -CO-(cyclohexenyl) 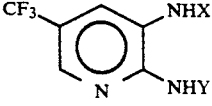 | —SO₂C₂H₅ | | 147~148 |
| 96 | -CO-(cyclohexenyl) 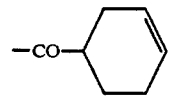 | —SO₂C₂H₅ | | 163~165 |
| 97 | -CO-(cycloheptyl) 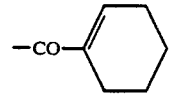 | —SO₂C₂H₅ | | 163~166 |
| 98 | -CO-(2-F-phenyl) 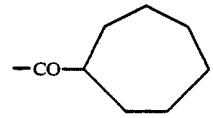 | —SO₂C₂H₅ | | 204~208 |
| 99 | -CO-(3-CF₃-phenyl) 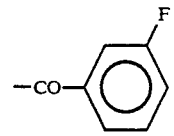 | —SO₂C₂H₅ | | 215~218 |
| 100 | -CO-(4-CF₃-phenyl) 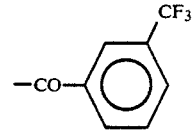 | —SO₂C₂H₅ | | 233~237 |
| 101 | -CO-(2-furyl) 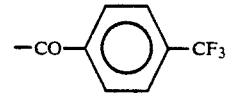 | —SO₂C₂H₅ | | 208~209 |
| 102 | -CO-(indanyl) 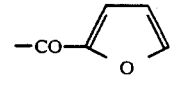 | —SO₂C₂H₅ | | 188~190 |
| 103 | -CO-(cyclohexyl) 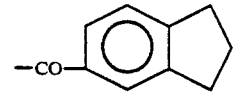 | —SO₂C₃H₇(iso) | | 152~154 |
| 104 | -CO-(2-F-phenyl) 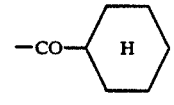 | —SO₂C₃H₇(iso) | | 216~217 |
| 105 | -CO-(4-Cl-phenyl) 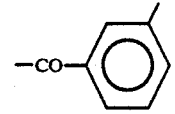 | —SO₂C₃H₇(iso) | | 227~230 |
| 106 | —COOC₃H₇(n) | —SO₂C₃H₇(iso) | | 161~163 |

TABLE 5-continued
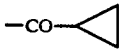
(I)
| Compound No. | X | Y | Type of salt | Melting point (°C.) |
|---|---|---|---|---|
| 107 | 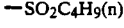 | —SO₂C₄H₉(n) | | 138~139 |
| 108 | —COCF₂Cl | —SO₂C₄H₉(n) | | 156 |
| 109 |  |  | | 202~205 |
| 110 | —CO(CH₂)₄CH₃ | —SO₂N(CH₃)₂ | | 97 |
| 111 | 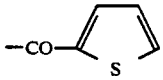 | —SO₂N(CH₃)₂ | | 168~169 |
| 112 | —COCF₂CF₃ | —SO₂N(CH₃)₂ | | 157~159 |
| 113 | 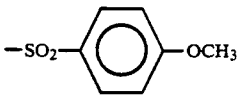 | —SO₂N(CH₃)₂ | | 189~191 |
| 114 | —COOC₃H₇(n) | —SO₂N(CH₃)₂ | | 174~176 |
| 115 |  | —SO₂OCH₃ | | 147~148 |
| 116 | 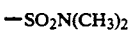 | —SO₂OCH₃ | | 163~164 |
| 117 | 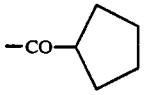 | —SO₂OC₂H₅ | | 140~141 |
| 118 | 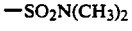 | —SO₂OC₂H₅ | | 160~162 |
| 119 |  | —SO₂C₂H₅ | | 137~139 |
| 120 | 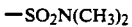 | —SO₂CH₃ | | 202~203 |
| 121 | 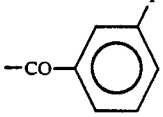 | —SO₂CH₃ | | 145~147 |

TABLE 5-continued $$\text{CF}_3\text{-pyridine with NHX, NHY substituents} \quad (I)$$

| Compound No. | X | Y | Type of salt | Melting point (°C.) |
|---|---|---|---|---|
| 122 | —CO—(2,5-dimethylphenyl) | —SO$_2$CH$_3$ | | 221~224 |
| 123 | —CO—(5,6,7,8-tetrahydronaphthalen-2-yl) | —SO$_2$CH$_3$ | | 184~185 |
| 124 | —CO(CH$_2$)$_5$CH$_3$ | —SO$_2$CH$_3$ | | 94~96 |
| 125 | —CO(CH$_2$)$_6$CH$_3$ | —SO$_2$CH$_3$ | | 94~96 |
| 126 | —CO—cyclohexyl | —SO$_2$—(2-thienyl) | | 178~180 |
| 127 | —CO—(indanyl) | —SO$_2$—(2-thienyl) | | 226~228 |
| 128 | —C(O)—C(O)—OC$_2$H$_5$ | —SO$_2$CH$_3$ | | |
| 129 | —C(O)—C(O)—O—phenyl | —SO$_2$CH$_3$ | | |
| 130 | —C(O)—OCH$_2$CH=CH$_2$ | —SO$_2$CH$_3$ | | |
| 131 | —C(O)—OCH$_2$C≡CH | —SO$_2$CH$_3$ | | |
| 132 | —C(O)—S—C$_2$H$_5$ | —SO$_2$CH$_3$ | | |
| 133 | —C(O)—cyclohexyl | —C(O)—O—phenyl | | |
| 134 | —C(O)—cyclohexyl | —NHSO$_2$O—phenyl | | |
| 135 | —C(O)—cyclohexyl | —SO$_2$O—phenyl | | |

TABLE 5-continued

Structure (I):
Pyridine with CF$_3$ at 5-position, NHX at 3-position, NHY at 2-position.

| Compound No. | X | Y | Type of salt | Melting point (°C.) |
|---|---|---|---|---|
| 136 | —C(=O)N(CH$_3$)CH$_3$ (N,N-dimethylcarbamoyl) | —SO$_2$C$_2$H$_5$ | | |
| 137 | —C(=O)—cyclohexyl | —NHSO$_2$N(CH$_3$)CH$_3$ | | |
| 138 | —C(=O)—cyclohexyl | —C(=O)—S—CH$_2$—C$_6$H$_5$ | | |
| 139 | —C(=O)—cyclohexyl | —SO$_2$CH$_2$—C(CH$_3$)=CH$_2$ | | 138~140 |
| 140 | —C(=O)—cyclohexyl | —SO$_2$—cyclohexyl | | 190~192 |
| 141 | —C(=O)—cyclohexyl | —SO$_2$—(2-naphthyl) | | |
| 142 | —C(=O)—(2-naphthyl) | —SO$_2$C$_2$H$_5$ | | 210~211 |
| 143 | —C(=O)—(tetrahydronaphthyl) | —SO$_2$C$_2$H$_5$ | | |
| 144 | —C(=O)—(indanyl) | —SO$_2$C$_2$H$_5$ | | |
| 145 | —C(=O)—cyclohexyl | —SO$_2$—(indanyl) | | |
| 146 | —C(=O)—(1-adamantyl) | —SO$_2$C$_2$H$_5$ | | |

TABLE 5-continued $$\text{(I)} \quad \underset{N}{\underset{\|}{\bigcirc}}\!\!\!\begin{array}{c}CF_3\\ \\ NHX\\ NHY\end{array}$$

| Compound No. | X | Y | Type of salt | Melting point (°C.) |
|---|---|---|---|---|
| 147 | -C(=O)-adamantyl | —SO$_2$C$_2$H$_5$ | | |
| 148 | -C(=O)-norbornyl | —SO$_2$C$_2$H$_5$ | | |
| 149 | -C(=O)-camphoryl | —SO$_2$C$_2$H$_5$ | | |
| 150 | -C(=O)-cyclohexyl (H) | -C(=O)-phenyl | | |
| 151 | -C(=O)-cyclohexyl (H) | —SO$_2$-indanyl | | |
| 152 | -C(=O)-(N-methylpyrrolyl) | —SO$_2$C$_2$H$_5$ | | |
| 153 | -C(=O)-cyclohexyl (H) | —SO$_2$-furyl | | |
| 154 | -C(=O)-cyclohexyl (H) | —SO$_2$-phenyl | | 166~167 |
| 155 | -C(=O)-cyclohexyl (H) | —SO$_2$-(4-COOC$_2$H$_5$-1-methylpyrazol-5-yl) | | 144~146 |
| 156 | -C(=O)-cyclohexyl (H) | —SO$_2$-(1-methylimidazolyl) | | |
| 157 | -C(=O)-(2-methyloxazol-4-yl) | —SO$_2$C$_2$H$_5$ | | |

TABLE 5-continued

Structure (I): pyridine with CF$_3$, NHX, NHY, N substituents

| Compound No. | X | Y | Type of salt | Melting point (°C.) |
|---|---|---|---|---|
| 158 | −CO−(3,5-dimethylisoxazol-4-yl) | −SO$_2$C$_2$H$_5$ | | |
| 159 | −CO−cyclohexyl (H) | −SO$_2$−(3,5-dimethylisoxazol-4-yl) | | |
| 160 | −CO−cyclohexyl (H) | −SO$_2$−(2,4-dimethylthiazol-5-yl) | | |
| 161 | −CO−(3-methylisothiazol-5-yl) | −SO$_2$C$_2$H$_5$ | | |
| 162 | −CO−cyclohexyl (H) | −SO$_2$−(3-methyl-5-(2,2,2-trifluoroethoxy)isothiazol-4-yl) | | 133~135 |
| 163 | −CO−(1,2,3-thiadiazol-4-yl) | −SO$_2$C$_2$H$_5$ | | |
| 164 | −CO−(3,4-dihydro-2H-pyrrol-5-yl) | −SO$_2$C$_2$H$_5$ | | |
| 165 | −CO−(1-methylpyrrolidin-2-yl) | −SO$_2$C$_2$H$_5$ | | |
| 166 | −CO−N(pyrrolidinyl) | −SO$_2$C$_2$H$_5$ | | |
| 167 | −CO−cyclohexyl (H) | −SO$_2$−N(pyrrolidinyl) | | |
| 168 | −CO−(4,5-dihydrofuran-2-yl) | −SO$_2$C$_2$H$_5$ | | |

TABLE 5-continued

(I)

| Compound No. | X | Y | Type of salt | Melting point (°C.) |
|---|---|---|---|---|
| 169 | [2,3-dihydrofuran-2-yl-carbonyl] | —SO$_2$C$_2$H$_5$ | | |
| 170 | [2,3-dihydrothiophene-2-yl-carbonyl] | —SO$_2$C$_2$H$_5$ | | |
| 171 | [tetrahydrothiophene-2-yl-carbonyl] | —SO$_2$C$_2$H$_5$ | | |
| 172 | [1-methyl-4,5-dihydropyrazol-3-yl-carbonyl] | —SO$_2$C$_2$H$_5$ | | |
| 173 | [1,3-dimethyl-2,5-dioxoimidazolidin-4-yl-carbonyl] | —SO$_2$C$_2$H$_5$ | | |
| 174 | [2-methyl-4,5-dihydrooxazol-4-yl-methylcarbonyl] | —SO$_2$C$_2$H$_5$ | | |
| 175 | [4,5-dihydroisoxazol-3-yl-carbonyl] | —SO$_2$C$_2$H$_5$ | | |
| 176 | [2-ethyl-3,4-dimethylisoxazolidin-4-yl-carbonyl] | —SO$_2$C$_2$H$_5$ | | |
| 177 | [4,5-dihydroisothiazol-4-yl-carbonyl] | —SO$_2$C$_2$H$_5$ | | |
| 178 | [3-methylthiazolidin-4-yl-carbonyl] | —SO$_2$C$_2$H$_5$ | | |
| 179 | [2,2-dimethyl-1,3-dioxolan-4-yl-methylcarbonyl] | —SO$_2$C$_2$H$_5$ | | |

TABLE 5-continued

Structure (I): pyridine with CF₃ at 5-position, NHX at 3-position, NHY at 2-position.

| Compound No. | X | Y | Type of salt | Melting point (°C.) |
|---|---|---|---|---|
| 180 | -C(=O)-CH(-S-C(CH₃)₂-S-CH₂-) (cyclic dithiane with gem-dimethyl) | -SO₂C₂H₅ | | |
| 181 | -C(=O)-(2-pyridyl with 5-CF₃) | -SO₂C₂H₅ | | |
| 182 | -C(=O)-(pyridazinyl) | -SO₂C₂H₅ | | |
| 183 | -C(=O)-(pyrimidinyl) | -SO₂C₂H₅ | | |
| 184 | -C(=O)-cyclohexyl (H) | -SO₂-(2-pyrimidinyl) | | |
| 185 | -C(=O)-(6-methyl-3-pyridyl) | -SO₂C₂H₅ | | |
| 186 | -C(=O)-cyclohexyl (H) | -SO₂-(pyrazinyl) | | |
| 187 | -C(=O)-(1-methyl-1,2,3,6-tetrahydropyridin-2-yl) | -SO₂C₂H₅ | | |
| 188 | -C(=O)-(1-methyl-1,2,3,6-tetrahydropyridin-4-yl) | -SO₂C₂H₅ | | |
| 189 | -C(=O)-(1-methylpiperidin-3-yl) | -SO₂C₂H₅ | | |

TABLE 5-continued

Structure (I): pyridine with CF$_3$ at 5-position, NHX at 3-position, NHY at 2-position.

| Compound No. | X | Y | Type of salt | Melting point (°C.) |
|---|---|---|---|---|
| 190 | −C(=O)−N(piperidinyl) | −SO$_2$C$_2$H$_5$ | | |
| 191 | −C(=O)−cyclohexyl | −SO$_2$−N(piperidinyl) | | |
| 192 | −C(=O)−(1-methyl-6-oxo-1,6-dihydropyridazin-5-yl) | −SO$_2$C$_2$H$_5$ | | |
| 193 | −C(=O)−(1-methyl-6-oxo-1,4,5,6-tetrahydropyridazin-5-yl) | −SO$_2$C$_2$H$_5$ | | |
| 194 | −C(=O)−(3-methyl-2-oxo-2,3-dihydropyrimidin-5-yl) | −SO$_2$C$_2$H$_5$ | | |
| 195 | −C(=O)−(2-oxo-1,2,3,4-tetrahydropyrimidin-5-yl) | −SO$_2$C$_2$H$_5$ | | |
| 196 | −C(=O)−(1,4-dimethylpiperazin-2-yl) | −SO$_2$C$_2$H$_5$ | | |
| 197 | −C(=O)−(3,4-dihydro-2H-pyran-5-yl) | −SO$_2$C$_2$H$_5$ | | |
| 198 | −C(=O)−(tetrahydro-2H-pyran-3-yl) | −SO$_2$C$_2$H$_5$ | | |

TABLE 5-continued $$\text{(I)} \quad \underset{N}{\overset{CF_3}{\bigcirc}} \overset{NHX}{\underset{NHY}{}}$$

| Compound No. | X | Y | Type of salt | Melting point (°C.) |
|---|---|---|---|---|
| 199 | -C(=O)-[1,3-dioxan-2-yl] | -SO₂C₂H₅ | | |
| 200 | -C(=O)-[1,4-dithiin-2-yl] | -SO₂C₂H₅ | | |
| 201 | -C(=O)-[1,3-dithian-2-yl] | -SO₂C₂H₅ | | |
| 202 | -C(=O)-N(morpholino) | -SO₂C₂H₅ | | |
| 203 | -C(=O)-cyclohexyl(H) | -SO₂-N(morpholino) | | |
| 204 | -C(=O)-(N-methylmorpholin-3-yl) | -SO₂C₂H₅ | | |
| 205 | -C(=O)-(thieno[3,2-b]thiophen-2-yl) | -SO₂C₂H₅ | | |
| 206 | -C(=O)-(1-methylindol-2-yl) | -SO₂C₂H₅ | | |
| 207 | -C(=O)-(benzofuran-2-yl) | -SO₂C₂H₅ | | 265~266 |
| 208 | -C(=O)-cyclohexyl(H) | -SO₂-(3-methylbenzofuran-2-yl) | | |

TABLE 5-continued (I) structure: pyridine with CF₃ at 5-position, NHX at 3-position, NHY at 2-position (N in ring).

| Compound No. | X | Y | Type of salt | Melting point (°C.) |
|---|---|---|---|---|
| 209 | -C(=O)-(2-chloro-benzoxazol-5-yl) | —SO₂C₂H₅ | | |
| 210 | -C(=O)-(benzo[d]isoxazol-3-yl) | —SO₂C₂H₅ | | |
| 211 | -C(=O)-(5-methoxy-benzothiazol-2-yl) | —SO₂C₂H₅ | | |
| 212 | -C(=O)-cyclohexyl | —SO₂-(benzothiazol-2-yl) | | |
| 213 | -C(=O)-(1-methyl-benzimidazol-2-yl) | —SO₂C₂H₅ | | |
| 214 | -C(=O)-(4,5,6,7-tetrahydrobenzothiophen-2-yl) | —SO₂C₂H₅ | | 248~249 |
| 215 | -C(=O)-(2,3-dihydrobenzofuran-5-yl) | —SO₂C₂H₅ | | |
| 216 | -C(=O)-(4,5,6,7-tetrahydrobenzo[d]isoxazol-3-yl) | —SO₂C₂H₅ | | |
| 217 | -C(=O)-(benzo[d][1,3]dioxol-5-yl) | —SO₂C₂H₅ | | 219~221 |
| 218 | -C(=O)-(quinolin-3-yl) | —SO₂C₂H₅ | | 241~242 |
| 219 | -C(=O)-cyclohexyl | —SO₂-(quinolin-8-yl) | | |

TABLE 5-continued $$\underset{\text{(I)}}{\overset{CF_3}{\underset{N}{\bigwedge}}\overset{NHX}{\underset{NHY}{}}}$$

| Compound No. | X | Y | Type of salt | Melting point (°C.) |
|---|---|---|---|---|
| 220 | -C(=O)-(isoquinolin-3-yl) | -SO$_2$C$_2$H$_5$ | | |
| 221 | -C(=O)-cyclohexyl (H shown) | -SO$_2$-(2,3-dihydro-1,4-benzodioxin-6-yl) | | |
| 222 | -C(=O)-(quinoxalin-2-yl) | -SO$_2$C$_2$H$_5$ | | |
| 223 | -C(=O)-(quinuclidin-2-yl) | -SO$_2$C$_2$H$_5$ | | |
| 224 | -C(=S)-C$_6$H$_5$ | -SO$_2$C$_2$H$_5$ | | |
| 225 | -C(=O)-CH$_2$-OCH$_2$CF$_3$ | -SO$_2$C$_2$H$_5$ | | |
| 226 | -C(=O)-CH$_2$SCH$_3$ | -SO$_2$C$_2$H$_5$ | | |
| 227 | -C(=O)-CH$_2$O-cyclopentyl | -SO$_2$C$_2$H$_5$ | | |
| 228 | -C(=O)CH$_2$O-cyclopent-2-enyl | -SO$_2$C$_2$H$_5$ | | |
| 229 | -C(=O)CH$_2$-O-cyclohexyl | -SO$_2$C$_2$H$_5$ | | |
| 230 | -C(=O)CH$_2$COOCH$_3$ | -SO$_2$C$_2$H$_5$ | | |
| 231 | -C(=O)(CH$_2$)$_2$C(=O)CH$_3$ | -SO$_2$C$_2$H$_5$ | | |
| 232 | -C(=O)CH=CH-(furan-2-yl) | -SO$_2$C$_2$H$_5$ | | |

TABLE 5-continued $$\text{(I)}\quad \underset{N}{\overset{CF_3}{\underset{\displaystyle}{\bigotimes}}}\!\!\begin{array}{c}NHX\\NHY\end{array}$$

| Compound No. | X | Y | Type of salt | Melting point (°C.) |
|---|---|---|---|---|
| 233 | −C(O)CH$_2$−(2-pyridyl) | −SO$_2$C$_2$H$_5$ | | |
| 234 | −C(O)CH$_2$O−(2-naphthyl) | −SO$_2$C$_2$H$_5$ | | |
| 235 | −C(O)CH$_2$S−(benzofuran-3-yl) | −SO$_2$C$_2$H$_5$ | | |
| 236 | −C(O)CH$_2$O−(benzothiophen-yl) | −SO$_2$C$_2$H$_5$ | | |
| 237 | −C(O)CH$_2$S−(quinolin-8-yl) | −SO$_2$C$_2$H$_5$ | | |
| 238 | −C(O)CH$_2$N(CH$_3$)$_2$ | −SO$_2$C$_2$H$_5$ | | |
| 239 | −C(O)−C$_6$H$_4$−SCH$_3$ (4-) | −SO$_2$C$_2$H$_5$ | | |
| 240 | −C(O)−C$_6$H$_4$−N(CH$_3$)$_2$ (4-) | −SO$_2$C$_2$H$_5$ | | |
| 241 | −C(O)−C$_6$H$_4$−CN (4-) | −SO$_2$C$_2$H$_5$ | | |
| 242 | −C(O)−C$_6$H$_4$−NO$_2$ (4-) | −SO$_2$C$_2$H$_5$ | | |
| 243 | −C(O)−C$_6$H$_4$−COOCH$_3$ (4-) | −SO$_2$C$_2$H$_5$ | | |

TABLE 5-continued $$\underset{N}{\underset{\|}{\text{CF}_3}} \overset{\text{NHX}}{\underset{\text{NHY}}{\bigotimes}} \quad (I)$$

| Compound No. | X | Y | Type of salt | Melting point (°C.) |
|---|---|---|---|---|
| 244 | −CO−C₆H₄−OCOCH₃ (para) | −SO₂C₂H₅ | | |
| 245 | −CO−C₆H₄−COCH₃ (para) | −SO₂C₂H₅ | | |
| 246 | −CO−cyclohexyl | −SO₂CH₂−C₆H₅ | | |
| 247 | −CO−CH₂−O−CH(CH₃)−O−CH(CH₃)− (dioxane with isopropyl) | −SO₂C₂H₅ | | |
| 248 | −CO−cyclohexyl | −SO₂−(2-pyridyl) | | |
| 249 | −CO−cyclohexyl | −SO₂C₃H₇(n) | | |
| 250 | −CO−(5,6,7,8-tetrahydronaphth-2-yl) | −SO₂C₃H₇(n) | | |
| 251 | −CO−cyclohexyl | SO₂C₂H₅ | Na salt | 299 (decomposed) |
| 252 | −CO−cyclohexyl | SO₂C₂H₅ | K salt | More than 300 |
| 253 | −CO−cyclohexyl | SO₂C₃H₇(iso) | Na salt | |
| 254 | −CO−cyclohexyl | SO₂CF₃ | Na salt | |
| 255 | −CO−cyclohexyl | SO₂−C₆H₅ | Na salt | |

TABLE 5-continued $$\text{(I)}$$

Structure: pyridine ring with CF$_3$, NHX, NHY, N substituents

| Compound No. | X | Y | Type of salt | Melting point (°C.) |
|---|---|---|---|---|
| 256 | —CO—(cyclopentyl) | SO$_2$C$_2$H$_5$ | Na salt | |
| 257 | —CO—(2-fluorophenyl) | SO$_2$C$_2$H$_5$ | Na salt | |
| 258 | —CO—(cyclohexenyl) | SO$_2$C$_2$H$_5$ | Na salt | |
| 259 | —CO—(4-fluorophenyl) | —SO$_2$CH$_3$ | Na salt | More than 300 |
| 260 | —COCF$_2$CF$_3$ | —SO$_2$CH$_3$ | Na salt | More than 300 |
| 261 | —COCF$_2$CF$_3$ | —SO$_2$C$_2$H$_5$ | Na salt | |
| 262 | —CO—(cyclohexyl, H) | —SO$_2$C$_2$H$_5$ | Ca salt | 245 (decomposed) |

The compound of the formula (I) of the present invention is useful as an active ingredient for a phospholipase A$_2$ inhibitor, an anti-inflammatory agent or an anti-pancreatitis agent. Phospholipase A$_2$ can be detected in various tissues or cells in a body. It is said that in platelets or cells related to inflammatory symptoms, phospholipase A$_2$ is secreted or activated by various stimulations and contributes to the production of a platelet activating factor (PAF) or some arachidonic acid methabolites. The arachidonic acid methabolites have been found to be closely related to various diseases, for example, inflammatory symptoms such as rheumatoid arthritis, arthritis deformans, tenontitis, psoriasis and related dermatitis; nasal and bronchial airway troubles such as allergic rhinitis and allergic bronchial asthma; and immediate hypersensitive reactions such as allergic conjunctivitis. On the other hand, phospholipase A$_2$ secreted from pancreas is activated in the intestine and exhibits a digestive action, but once activated in the pancreas, it is believed to be one of the factors causing pancreatitis. The compound of the present invention inhibits phospholipase A$_2$ and thus is effective for the treatment of the above-mentioned diseases caused by phospholipase A$_2$ such as inflammatory symptoms, nasal and bronchial airway troubles, immediate hypersensitive reactions or pancreatitis. Thus, it is useful as an anti-inflammatory agent, an agent for treating bronchial asthma, an anti-allergy agent, an anti-pancreatitis agent, anti-nephritis agent, or anti-MOFC (Multiple Organ Failure).

In regard to the efficacy against pancreatitis, the compound of the present invention is expected to be more efficient by using in combination with other drugs, for example, a proteinase inhibitor, such as galexate mesilate, camostat mesilate, or nafamostat mesilate.

The compound of the present invention is particularly suitable for use as an anti-inflammatory agent and/or an anti-pancreatitis agent.

TEST EXAMPLE 1

Phospholipase A$_2$ inhibitory activity, method A (1) Preparation of substrate

To 10 mg of egg yolk lecithin (manufactured by Wako Pure Chemical Industries Ltd.), 1 ml of glycerine, 2 ml of a 50 mM Tris-HCl buffer solution (pH7.5) [Tris(hydroxymethyl)aminomethane (manufactured by Nacalai Tesque K.K.) was adjusted to pH7.5 with hydrochloric acid], 0.5 ml of a 150 mM calcium chloride solution (calcium chloride was dissolved in a 50 mM Tris-HCl buffer solution) and 0.5 ml of a 0.05% Triton-X100 (manufactured by Nacalai Tesque K.K.) solution (Triton-X100 was dissolved in a 50 mM Tris-HCl buffer solution), were added and dispersed by an agate mortar or dispersed by an ultrasonic processor (Model W-225, manufactured by Heat System-Ultrasonics, Inc.) for 5 minutes (30W) to obtain a substrate.

(2) Enzyme

Porcine pancreatic phospholipase A₂ [(161454.122416) manufactured by Boehringer Mannheim.Yamanouchi K.K.] was used.

(3) Measurement of phospholipase A₂ activity

To a 96 well microtitration plate (flat bottom, manufactured by Sumitomo Bakelite Medical Co., Ltd.), 40 μl of the substrate, 5 μl of a solution prepared by dissolving 10 mg of a test compound in 500 μl of dimethylsulfoxide, followed by an addition of 500 μl of a 50 mM Tris-HCl buffer solution, and 5 μl of an enzyme solution of 20 ng/ml (prepared by diluting the enzyme in a 50 mM Tris-HCl buffer solution), were added and reacted at 37° C. for 30 minutes. After termination of the reaction, the released free fatty acid was quantitatively analyzed in accordance with the ACS-ACOD (acyl CoA synthetase-acyl CoA oxidase) method [a kit of NEFA C test wako (manufactured by Wako Pure Chemical Industries, Ltd.) was used]. The quantitative analysis was made by means of Microplate ELISA Reader (Model 2550EIA Reader, manufactured by Bio-Rad Laboratories) at a wavelength of 540 nm. Separately, such experiments as mentioned above, were carried out at various concentrations (2 μg/ml, 1 μg/ml and 0.5 μg/ml) of phospholipase A₂ without a test compound. Then, the concentration of the free fatty acid versus the concentration of phospholipase A₂ was plotted.

From this standard curve, the apparent concentration of phospholipase A₂ in the case with a test compound, was read. Then, the percent inhibition of the enzyme was calculated by the following formula. The results are shown in Table 6.

$$\text{Percent inhibition (\%)} = \left(1 - \frac{A}{B}\right) \times 100$$

A: Apparent enzyme concentration when a test compound is added.
B: True enzyme concentration when a test compound is added.

TABLE 6

| Compound No. | % inhibition of PLA₂ (1,000 ppm) |
|---|---|
| 1 | 45 |
| 2 | 55 |
| 3 | 67 |
| 4 | 74 |
| 5 | 39 |
| 8 | 81 |
| 9 | 71 |
| 10 | 60 |
| 11 | 52 |
| 12 | 89 |
| 13 | 87 |
| 14 | 54 |
| 15 | 62 |
| 16 | 43 |
| 17 | 46 |
| 18 | 64 |
| 19 | >90 |
| 20 | 74 |
| 21 | 62 |
| 22 | 74 |
| 23 | 37 |
| 24 | 66 |
| 26 | 35 |
| 27 | 62 |
| 28 | 71 |

TABLE 6-continued

| Compound No. | % inhibition of PLA₂ (1,000 ppm) |
|---|---|
| 29 | 47 |
| 30 | 87 |
| 32 | 50 |
| 38 | 35 |
| 39 | 41 |
| 41 | 89 |
| 43 | 47 |
| 44 | 43 |
| 45 | 50 |
| 46 | 47 |
| 47 | 75 |
| 48 | 48 |
| 49 | 30 |
| 50 | 78 |
| 51 | 63 |
| 52 | 49 |
| 53 | 37 |
| 54 | 37 |
| 55 | 49 |
| 57 | 57 |
| 58 | 74 |

TEST EXAMPLE 2

Phospholipase A₂ inhibitory activity, method B

(1) Preparation of substrate

To a solution prepared by dissolving 9.2 mg of L-α-dipalmitoylphosphatidylcholine (manufactured by Nichiyu Liposome K.K.) in 0.5 ml of chloroform, a solution prepared by dissolving 32 mg of sodium cholate (manufactured by Wako Pure Chemical Industries, Ltd.) in 0.5 ml of methanol, was added, followed by mixing. The solvent of the mixture was removed under a nitrogen stream, and then 2.5 ml of a 250 mM sodium chloride solution [prepared by dissolving sodium chloride in a 100 mM Tris-HCl buffer solution {tris(hydroxymethyl)aminomethane (manufactured by Nacalai Tesque K.K.) was adjusted to pH8.0 with hydrochloric acid}] was added thereto, and the mixture was dissolved under stirring to obtain a substrate.

(2) Enzyme

Porcine pancreatic phospholipase A₂ [(161454.122416) manufactured by Boehringer Mannheim.Yamanouchi K.K.]was used.

(3) Measurement of phospholipase A₂ activity

To a 96 well microtitration plate, 20 μl of a solution containing calcium chloride, bovine serum alubmin (manufactured by Sigma Chemical, Co.) and a Tris-HCl buffer solution (pH8.0) at concentrations of 25 mM, 4.5 mg/ml and 100 mM, respectively, 5 μl of a solution prepared by dissolving 10 mg of a test compound in 500 μl of diemthylsulfoxide, followed by an addition of 500 μl of a 200 mM Tris-HCl buffer solution, 5 μl of an enzyme solution (10 μg/ml) [prepared by dissolving the enzyme in a bovine serum alubmin solution (prepared by dissolving bovine serum alubmin in a 100 mM Tris-HCl buffer solution at a concentration of 1 mg/ml)] and 20 μl of the substrate, were added and reacted at 37° C. for 30 minutes. After termination of the reaction, the released free fatty acid was quantitatively analyzed in accordance with the ACS-ACOD (acyl CoA synthetase-acyl CoA oxidase) method [a kit of NEFA C test wako (manufactured by Wako Pure Chemical Industries, Ltd.) was used]. The quantitative analysis was made by means of Microplate ELISA Reader (Model 2550EIA Reader, manufactured by Bio-Rad Laboratories) at a wavelength of 540 nm. Separately, such experiments as mentioned above, were carried out at various concentrations (1 μg/ml, 0.75 μg/ml, 0.5 μg/mol and 0.25 μg/ml) of phospholipase $A_2$ without a test compound. Then, the concentration of the free fatty acid versus the concentration of phospholipase $A_2$ was plotted.

From this standard curve, the apparent concentration of phospholipase $A_2$ in the case with a test compound, was read. Then, the percent inhibition of the enzyme was calculated by the following formula. The results are shown in Table 7.

$$\text{Percent inhibition (\%)} = \left(1 - \frac{A}{B}\right) \times 100$$

A: Apparent enzyme concentration when a test compound is added.

B: True enzyme concentration when a test compound is added.

TABLE 7

| Compound No. | % inhibition of $PLA_2$ (1,000 ppm) |
|---|---|
| 7 | 50 |
| 10 | 51 |
| 13 | 51 |
| 18 | 49 |
| 19 | 75 |
| 43 | 49 |
| 44 | 64 |
| 45 | 41 |
| 47 | 90 |
| 53 | 100 |
| 58 | 42 |
| 60 | 41 |
| 61 | 36 |
| 62 | 53 |
| 63 | 34 |
| 64 | 61 |
| 65 | 71 |
| 66 | 52 |
| 67 | 82 |
| 68 | 81 |
| 69 | 63 |
| 70 | 40 |
| 71 | 77 |
| 72 | 73 |
| 73 | 53 |
| 74 | 33 |
| 75 | 81 |
| 76 | 61 |
| 77 | 61 |
| 78 | 51 |
| 79 | 65 |
| 80 | 73 |
| 81 | 94 |
| 82 | 38 |
| 83 | 64 |
| 84 | 56 |
| 85 | 33 |
| 86 | 93 |
| 87 | 88 |
| 88 | 83 |
| 89 | 51 |
| 90 | 79 |
| 91 | 81 |
| 92 | 75 |
| 93 | 48 |
| 94 | 63 |
| 95 | 85 |
| 97 | 88 |
| 98 | 65 |
| 99 | 86 |

TABLE 7-continued

| Compound No. | % inhibition of $PLA_2$ (1,000 ppm) |
|---|---|
| 100 | 83 |
| 103 | 86 |
| 104 | 61 |
| 106 | 78 |
| 108 | 61 |
| 109 | 67 |
| 110 | 58 |
| 111 | 41 |
| 112 | 79 |
| 113 | 35 |
| 114 | 53 |
| 115 | 52 |
| 116 | 69 |
| 117 | 65 |
| 118 | 84 |
| 121 | 90 |
| 122 | 56 |
| 123 | 86 |
| 124 | 78 |
| 125 | 86 |
| 126 | 84 |
| 127 | 89 |
| 251 | 85 |
| 259 | 61 |
| 260 | 53 |

TEST EXAMPLE 3

Inhibitory activity on increased vascular permeability induced by acetic acid (Mouse Whittle method, method C Using ddy male mice, each test group consisted of 4 or 5 mice. A test compound was mixed with Tween 80 [polyoxyethylenesorbitan monooleate (manufactured by Nacalai Tesque K.K.)], and distilled water was added thereto to obtain a 2% Tween 80 suspension, or it was dissolved in the form of a salt in water to obtain an aqueous solution. A test compound was orally administered, and upon expiration of one hour from the administration, 0.7% acetic acid was intraperitonially injected to each mouse in an amount of 0.1 ml/10 g, and at the same time, 2% brilliant blue was intravenously injected into the tail vein in an amount of 0.1 ml/20 g. Thirty minutes after the injection of brilliant blue, the cervical vertebrae were dislocated under anesthesia by chloroform, and the abdorminal cavity was washed with 5 ml of a physiological saline. The washing solution was subjected to centrifugal separation at 3,000 rpm for 10 minutes, and the amount of the dye in the supernatant was measured at 600 nm absorbance by Microplate ELISA Reader (Model 2550EIA Reader, manufactured by Bio-Rad Laboratories). The inhibition rate of the amount of leaked dye in the group in which a test compound was administered relative to the control group was obtained by the following formula. The results are shown in Table 8.

$$\text{Inhibition rate (\%)} = \left(1 - \frac{C}{D}\right) \times 100$$

C: Amount of leaked dye in the group to which a test compound was administered.

D: Amount of leaked dye in the control group.

TABLE 8

| Compound No. | Dose (mg/kg) | Inhibition rate (%) |
|---|---|---|
| 1 | 50 | 46 |
| 2 | 20 | 51 |
| 3 | 50 | 58 |
| 4 | 50 | 43 |
| 5 | 50 | 53 |
| 7 | 20 | 53 |
| 8 | 20 | 48 |
| 9 | 50 | 81 |
| 10 | 25 | 53 |
|  | 10 | 42 |
| 11 | 100 | 49 |
| 13 | 100 | 57 |
| 15 | 50 | 41 |
| 16 | 20 | 55 |
| 17 | 50 | 31 |
| 18 | 25 | 49 |
| 20 | 20 | 48 |
| 22 | 20 | 81 |
|  | 10 | 39 |
| 23 | 20 | 33 |
| 39 | 20 | 53 |
| 41 | 100 | 85 |
| 43 | 20 | 48 |
| 45 | 20 | 29 |
| 47 | 20 | 72 |
|  | 10 | 46 |
| 49 | 20 | 50 |
| 55 | 25 | 59 |
| 57 | 20 | 43 |
| 63 | 10 | 41 |
| 78 | 20 | 51 |
|  | 10 | 32 |
| 79 | 20 | 67 |
| 86 | 20 | 42 |
| 87 | 10 | 28 |
| 93 | 20 | 47 |
|  | 10 | 40 |
| 94 | 20 | 53 |
| 101 | 20 | 46 |
| 120 | 20 | 43 |
| 251 | 20 | 43 |

TEST EXAMPLE 4

Inhibitory-activity on increased vascular permeability induced by acetic acid (Rat Whittle method, method D Using SD (Crj: CD) male rats, each test group consisted of from 3 to 5 rats. A test compound was mixed with Tween 80 [polyoxyethylenesorbitan monooleate (manufactured by Nacalai Tesque K.K.)], and distilled water was added thereto to obtain a 2% Tween 80 suspension, or it was dissolved in the form of a salt in water to obtain an aqueous solution. A test compound was orally administered, and one hour later, 0.7% acetic acid was intraperitonially injected to each rat in an amount of 0.05 ml/10 g, and at the same time, 2% brilliant blue was intravenously injected into the tail vein in an amount of 0.05 ml/20 g. Thirty minutes after the injection of brilliant blue, the cervical vertebrae were dislocated under anesthesia by chloroform, and the abdorminal cavity was washed with 10 ml of a physiological saline. The washing solution was subjected to centrifugal separation at 3,000 rpm for 10 minutes, and the amount of the dye in the supernatant was measured at 600 nm absorbance by Microplate ELISA Reader (Model 2550EIA Reader, manufactured by Bio-Rad Laboratories). The inhibition rate of the amount of leaked dye in the group to which a test compound was administered relative to the control group was obtained from the following formula, and the results are shown in Table 9.

$$\text{Inhibition rate (\%)} = \left(1 - \frac{C}{D}\right) \times 100$$

C: Amount of leaked dye in the group to which a test compound was administered.
D: Amount of leaked dye in the control group.

TABLE 9

| Compound No. | Dose (mg/kg) | Inhibition rate (%) |
|---|---|---|
| 2 | 100 | 38 |
| 3 | 100 | 75 |
| 10 | 100 | 57 |
|  | 50 | 37 |
| 16 | 100 | 96 |
| 17 | 50 | 40 |
| 19 | 50 | 34 |
| 20 | 100 | 49 |
| 22 | 100 | 58 |
| 23 | 100 | 40 |
| 43 | 50 | 72 |
| 45 | 50 | 27 |
| 46 | 50 | 31 |
| 47 | 50 | 82 |
|  | 25 | 56 |
| 49 | 50 | 30 |
| 55 | 25 | 69 |
|  | 12.5 | 43 |
| 57 | 50 | 47 |
| 58 | 50 | 31 |
| 60 | 50 | 72 |
| 61 | 25 | 61 |
| 63 | 50 | 39 |
|  | 25 | 31 |
| 66 | 25 | 72 |
| 69 | 25 | 48 |
| 72 | 25 | 66 |
| 78 | 50 | 55 |
|  | 25 | 40 |
| 79 | 50 | 74 |
| 80 | 50 | 35 |
|  | 25 | 33 |
| 82 | 25 | 38 |
| 86 | 50 | 37 |
| 87 | 25 | 61 |
|  | 12.5 | 47 |
| 93 | 50 | 71 |
|  | 25 | 54 |
| 94 | 50 | 55 |
|  | 25 | 45 |
| 98 | 50 | 32 |
| 101 | 50 | 41 |
| 113 | 50 | 67 |
| 120 | 100 | 56 |
|  | 50 | 35 |
| 121 | 12.5 | 31 |
| 251 | 25 | 70 |
|  | 12.5 | 46 |

TEST EXAMPLE 5

Inhibitory activity on carrageenin edema

Using Wister male rats (body weight: about 100 g), each test group consisted of 5 rats. A test compound was mixed with Tween 80 [polyoxyethylenesorbitan monooleate (manufactured by Nacalai Tesque K.K.)], and distilled water was added thereto to obtain a 2% Tween 80 suspension, or it was dissolved in the form of a salt in water to obtain an aqueous solution. Either the suspension or the aqueous solution was orally administered in an amount of 200 mg/kg, 100 mg/kg, 50 mg/kg or 25 mg/kg. One hour later, 0.1 ml of a 1% λ-carrageenin solution dissolved in a physiological saline was injected subcutaneously to the right hind paw of each rat to cause inflamation. Three hours later, the paw volume was measured by a paw volume measuring device (manufactured by Ugobasiee K.K.). A swelling volume was obtained from the difference from the value before the inflammation. The inhibition rate was calculated by the following formula, and the results are shown in Table 10.

$$\text{Inhibition rate (\%)} = \left(1 - \frac{F}{E}\right) \times 100$$

F: Average swelling volume in the group to which a test compound was administered.
E: Average swelling volume in the control group.

TABLE 10

| Compound No. | Dose (mg/kg) | Inhibition rate (%) |
|---|---|---|
| 2 | 100 | 17 |
| 3 | 100 | 20 |
| 5 | 100 | 37 |
| 10 | 100 | 28 |
| 11 | 100 | 24 |
| 13 | 100 | 21 |
| 16 | 100 | 24 |
| 19 | 100 | 31 |
| 22 | 100 | 29 |
| 23 | 100 | 30 |
| 25 | 200 | 27 |
| 28 | 50 | 25 |
| 39 | 100 | 25 |
| 43 | 50 | 31 |
| 45 | 50 | 23 |
| 46 | 50 | 30 |
| 47 | 50 | 41 |
| 57 | 100 | 35 |
| 60 | 50 | 27 |
| 65 | 50 | 37 |
| 66 | 50 | 31 |
| 67 | 25 | 19 |
| 69 | 50 | 25 |
| 72 | 25 | 21 |
| 73 | 50 | 20 |
| 77 | 50 | 22 |
| 78 | 50 | 26 |
| 79 | 50 | 20 |
| 80 | 50 | 29 |
| 82 | 50 | 19 |
| 86 | 50 | 27 |
| 87 | 50 | 21 |
| 91 | 50 | 23 |
| 93 | 50 | 22 |
| 94 | 50 | 23 |
| 98 | 50 | 45 |
| 101 | 50 | 24 |
| 104 | 50 | 48 |
| 106 | 50 | 19 |
| 110 | 50 | 25 |
| 113 | 50 | 26 |
| 114 | 50 | 28 |
| 120 | 50 | 27 |
| 123 | 50 | 42 |
| 125 | 50 | 22 |
| 150 | 50 | 23 |
| 251 | 50 | 30 |
| 259 | 50 | 17 |

TEST EXAMPLE 6

Acute toxicity

Administration route: Intravenous injection

Using ddy male mice (body weight: 25-30 g), each test group consisted of 5 mice. A test compound was dissolved in the form of a sodium salt in a physiological saline or in a 5% glucose aqueous solution, and intravenously injected in an amount of 0.1 ml/10 g body weight. After the injection, the mortality rate was obtained over one week, and the median lethal dose $LD_{50}$ (mg/kg) was determined. The results are shown in Table 11.

TABLE 11

| Compound No. | $LD_{50}$ (mg/kg) |
|---|---|
| 1 | 100~150 |
| 2 | 50~100 |
| 3 | >100 |
| 8 | >25 |
| 9 | >150 |
| 10 | 50~100 |
| 11 | >150 |
| 12 | >150 |
| 13 | >70 |
| 15 | 100~150 |
| 16 | >100 |
| 17 | 50~100 |
| 18 | >150 |
| 19 | 50~100 |
| 21 | >75 |
| 22 | >100 |
| 24 | >150 |
| 40 | 50~100 |
| 43 | 78 |
| 45 | 98 |
| 47 | 58 |
| 49 | 175 |
| 55 | 237 |
| 57 | 83 |
| 60 | >60 |
| 61 | >80 |
| 63 | >130 |
| 68 | >80 |
| 73 | >80 |
| 77 | >80 |
| 78 | >60 |
| 80 | >80 |
| 86 | >40 |
| 87 | 75 |
| 91 | >80 |
| 106 | >20 |
| 120 | 83 |
| 251 | 65 |

TEST EXAMPLE 7

Effects against acute pancreatitis

Using Crj-CD male rats (for Compound No. 19, rats having a body weight of from 371 to 484 g were used, and for Compound No. 10, rats having a body weight of from 444 to 574 g were used), each test group consisted of 3 rats. An experimental acute pancreatitis model was prepared by a closed duodenal loop method under anesthesia with halothane (manufactured by Hoechst Japan) and nitrous oxide (manufactured by Sumitomo Seika K.K.) applied by means of a general inhalation anesthesia machine (Model EM-2 and halothane evaporator F-Model). Then, Compound No. 19 or Compound No. 10 was continuously intravenously injected into the tail vein in an amount of 50 mg per kg or 40 mg per kg, respectively, at a rate of 0.05 ml per minute by means of a pump (Technicon AA II Proportioning Pump III, manufactured by Technicon Instruments Corporation). No injection was made to a control group. Gross pathological examination was conducted upon expiration of 6 hours after the ventrotomy in the case of the test group to which Compound No. 19 was administered, or upon expiration of 3 hours after the ventrotomy in the case of the test group to which Compound No. 10 was administered. As a result, as shown in the following Table 12, the groups to which the compounds of the present invention were administered, show distinct usefulness for treating acute pancreatitis.

TABLE 12

| Groups | Pancreatic hemorrhage Petechia | | Pancreatic edema | |
|---|---|---|---|---|
| | Grade | Distribution | Grade | Distribution |
| Control group (against the group to which Compound No. 19 was administered) | ++ | ++ | ++ | ++ |
| | ++ | ++ | +++ | ++ |
| | +++ | +++ | +++ | ++ |
| Group to which Compound No. 19 was administered | − | − | + | + |
| | − | − | ++ | ++ |
| | − | − | + | + |
| Control group (against the group to which Compound No. 10 was administered) | ++ | ++ | ++ | ++ |
| | + | + | ++ | ++ |
| | ± | ± | ++ | ++ |
| Group to which Compound No. 10 was administered | ± | ± | ± | ± |
| | − | − | + | + |
| | + | + | ++ | + |

Grade of pancreatic lesions
−: No significant lesions,
±: Minimal,
+: Light,
++: Moderate,
+++: Marked
Distribution of pancreatic lesions
−: No significant lesions,
±~+++: Focal-diffuse

TEST EXAMPLE 8

Effects against acute pancreatitis

Using Crj-CD male rats, each test group consisted of 3 rats. An experimental acute pancreatitis model was prepared by a closed duodenal loop method under anethesia with halothane (manufactured by Hoechst Japan) and nitrous oxide (manufactured by Sumitomo Seika K.K.) applied by a general inhalation anesthesia machine (Model EM2 and halothane evaporator F- Model). Each compound (subjected to the test in the form of a sodium salt) was continuously intravenously injected into the tail vein in an amount of 0.4 ml/100 g to 0.6 ml/100 g at a rate of 0.05 ml per minute by a pump (Technicon AA II Proportioning Pump III, manufactured by Technicon Instruments Corporation) or rapidly intravenously injected. No injection was made to a control group. Gross pathological examination was conducted upon expiration of 6 hours after the ventrotomy in the case of the group to which the compound was administered. With respect to each of four lesions among pancreatic lesions i.e. petechia, ecchymosis, pancreatic necrosis and abdominal fatty necrosis, the grade and the distribution of lesions were scored with five grades of 0, 0.5, 1, 2 and 3 (severe lesions are 3). The sum of all lesions was designated as scores of pancreatitis lesions, and the sum of the score of petechia and the score of ecchymosis only was designated as scores of hemorrhagic lesions. The pancreatitis inhibition rate (%) and the hemorrhage inhibition rate (%) were obtained by the following formulas, and the results are shown in Table 13.

$$\text{Pancreatitis inhibition rate (\%)} = \left(1 - \frac{H}{G}\right) \times 100$$

H: Scores of pancreatitis lesions of the group to which a test compound was administered.
G: Scores of pancreatitis lesions of the control group.

$$\text{Hemorrhage inhibition rate (\%)} = \left(1 - \frac{J}{I}\right) \times 100$$

J: Scores of hemorrhagic lesions of the group to which a test compound was administered.
I: Scores of hemorrhagic lesions of the control group.

TABLE 13

| Compound No. | Dose (mg/kg) | *1 | *2 |
|---|---|---|---|
| 1 | 10 | 66 | 49 |
| 2 | 26* | 46 | |
| 3 | 10 | 49 | 51 |
| 9 | 10 | 36 | 21 |
| 11 | 23* | 52 | |
| 13 | 23* | 100 | |
| 14 | 19* | 52 | |
| 15 | 10 | 45 | 61 |
| 16 | 20* | 52 | |
| 17 | 20* | 73 | |
| 21 | 27* | 57 | |
| 24 | 11* | 68 | |
| 34 | 10 | 30 | 30 |
| 35 | 10 | 35 | 35 |
| 43 | 20* | 81 | |
| 45 | 25* | 62 | |
| 46 | 46* | 36 | |
| 47 | 20* | 68 | |
| 49 | 42* | 68 | |
| 55 | 40* | 65 | |
| 57 | 20* | 60 | |
| 58 | 10 | 70 | 51 |
| 60 | 10 | 92 | 94 |
| 61 | 10 | 79 | 64 |
| 62 | 10 | 45 | 61 |
| 63 | 10 | 83 | 66 |
| 64 | 10 | 60 | 68 |
| 65 | 10 | 67 | 74 |
| 66 | 10 | 53 | 63 |
| 68 | 10 | 74 | 77 |
| 72 | 10 | 62 | 32 |
| 73 | 10 | 74 | 79 |
| 74 | 10 | 66 | 67 |
| 77 | 10 | 66 | 70 |
| 78 | 10 | 96 | 91 |
| 79 | 10 | 23 | 39 |
| 80 | 10 | 11 | 8 |
| 81 | 10 | 49 | 58 |
| 83 | 10 | 53 | 51 |
| 85 | 10 | 57 | 67 |
| 86 | 10 | 87 | 85 |
| 87 | 10 | 83 | 87 |
| 93 | 10 | 70 | 70 |
| 94 | 10 | 11 | 11 |
| 97 | 10 | 35 | 35 |
| 106 | 10 | 96 | 97 |
| 107 | 10 | 63 | 61 |
| 113 | 10 | 41 | 36 |
| 114 | 10 | 32 | 27 |
| 117 | 10 | 30 | 30 |
| 120 | 24* | 100 | |
| 122 | 10 | 51 | 51 |
| 123 | 10 | 56 | 56 |
| 124 | 10 | 51 | 51 |
| 251 | 10 | 79 | 80 |

Note:
Symbol * in the column for "Dose" indicates a case of continuous intravenous injection, and no symbol indicates a case of single intravenous injection.
*1: Inhibition rate of hemorrhagic lesions (%)
*2: Inhibition rate of pancreatitis lesions (%)

To administer the compound of the present invention for the treatment of the above-mentioned diseases caused by phospholipase $A_2$, it is formulated alone or together with a pharmaceutically acceptable carrier into a drug composition suitable for peroral, or parenteral administration, such as a tablet, a powder, a capsule, a granule, an injection drug, an ointment, an inhalant or a suppository, and it is administered in the form of such a drug formulation.

As a drug formulation suitable for peroral administration, a solid composition such as a tablet, a capsule, a powder, a granule or a troach; or a liquid composition such as a syrup suspension, may be mentioned. The solid composition such as a tablet, a capsule, a powder, a granule or a troach may contain a binder such as fine crystalline cellulose, gum arabic, tragacanth gum, gelatine or polyvinyl chloride; an excipient such as starch, lactose or carboxymethyl cellulose; a disintegrator such as arginic acid, corn starch or carboxymethyl cellulose; a lubricant such as magnesium stearate, light silicic anhydride or colloidal silicon dioxide; a sweetener such as sucrose; or a flavoring agent such as peppermint or methyl salicylate. The liquid composition such as a syrup or a suspension may contain sorbitol, gelatine, methyl cellulose, carboxymethyl cellulose, a vegetable oil such as a peanut oil, an emulsifier such as lecithin as well as a sweetener, a preservative, a colorant or a flavoring agent, as the case requires. Such a composition may be provided in the form of a dried formulation. These formulations preferably contain from 1 to 95% by weight of the active compound.

A drug formulation suitable for parenteral administration may, for example, be an injection drug. The injection drug may be prepared by dissolving the compound in the form of a salt in usual water for injection, or may be formulated into a formulation suitable for injection such as a suspension or an emulsion (in a mixture with a pharmaceutically acceptable oil or liquid). In such a case, it may contain benzyl alcohol as an antibacterial agent, ascorbic acid as an antioxidant, a pharmaceutically acceptable buffer solution or a reagent for adjusting the osmotic pressure. Such an injection drug preferably contains from 0.1 to 8% by weight of the active compound.

A drug formulation suitable for topical or per rectal administration may, for example, be an inhalant, an ointment or a suppository. The inhalant may be formulated by dissolving the compound of the present invention alone or together with a pharmaceutically acceptable inert carrier in an aerosol or nebulizer solution, or may be administered to the resiratory airway in the form of fine powder for inhalation. In the case of fine powder for inhalation, the particle size is usually not more than 50 μm, preferably not more than 10 μm. Such an inhalant may be used, if neccesary, in combination with other antiasthematic agent or bronchodilator.

An ointment may be prepared by a conventional method by an addition of a commonly employed base or the like. The ointment preferably contains from 0.1 to 30% by weight of the active compound.

The suppository may contain a carrier for formulation which is well known in this field, such as polyethylene glycol, lanolin, cacao butter or fatty acid triglyceride. The suppository preferably contains from 1 to 95% by weight of the active compound.

The above-mentioned drug compositions suitable for peroral, parenteral, topical or per rectal administration, may be formulated by conventional methods so that after administration to a patient, the active component will be rapidly discharged, gradually discharged or belatedly discharged.

The dose of the compound of the present invention varies depending upon the type of the compound, the administration-method, the condition of the patient or the animal to be treated. The optimum dose and the number of administration under a specific condition must be determined by the judgement of a competent doctor. Usually, however, a daily dose to an adult is from about 0.01 g to about 10 g, preferably from about 0.05 g to about 5 g. In the case of the above inhalation method, the dose of the compound of the present invention is preferably from about 0.01 mg to about 100 mg per administration.

Now, specific Formulation Examples of the phospholipase $A_2$ inhibitor, the anti-inflammatory agent or the anti-pancreatitis agent of the present invention will be given.

| FORMULATION EXAMPLE 1 (tablet) | |
|---|---|
| (1) Compound No. 30 | 200 mg |
| (2) Lactose | 150 mg |
| (3) Starch | 30 mg |
| (4) Magnesium stearate | 6 mg |

The above composition is tabletted so that the components (1) to (4) constitute one tablet.

| FORMULATION EXAMPLE 2 (powder or microgranule) | |
|---|---|
| (1) Compound No. 35 | 200 mg |
| (2) Sugar ester (DK ester F-160, manufactured by Daiichi Kogyo) | 180 mg |
| (3) Surfactant (Dekagreen 1-L, manufactured by Nikko Chemicals) | 15 mg |
| (4) Light silicic anhydride | 25 mg |

The component (1) is wet-pulverized in an aqueous solution containing 5% of the component (3). Then, 180 mg of the component (2) is added thereto, and the mixture is freeze-dried. The dried product is pulverized and mixed with the component (4).

The mixture is formed into a power or microgranule. Such a powder or microgranule may be sealed in a capsule to obtain a capsule drug.

| FORMULATION EXAMPLE 3 (hard gelatine capsule) | |
|---|---|
| (1) Sodium salt of Compound No. 10 | 250 mg |
| (2) Starch | 200 mg |
| (3) Magnesium stearate | 10 mg |

The components (1) to (3) is packed in a hard gelatine capsule to obtain a hard gelatine capsule drug.

| FORMULATION EXAMPLE 4 (injection drug) | |
|---|---|
| (1) Sodium salt of Compound No. 19 | 1 g |
| (2) Glucose | 10 g |
| (3) Distilled water for injection | 200 ml |

The components (1) to (3) are formulated into an injection drug in accordance with a usual method for preparation of an injection drug.

| FORMULATION EXAMPLE 5 (ointment for external skin application) | |
|---|---|
| (1) Sodium salt of Compound No. 10 | 5 g |
| (2) White vaseline | 25 g |
| (3) Stearyl alcohol | 22 g |
| (4) Propylene glycol | 12 g |
| (5) Sodium lauryl sulfate | 1.5 g |
| (6) Ethyl para-hydroxybenzoate | 0.025 g |
| (7) Propyl para-hydroxybenzoate | 0.015 g |
| (8) Purified water | 100 g |

The components (1) to (8) are formulated into an ointment for external skin application by a usual method for preparation of an ointment.

We claim:

1. A diaminotrifluoromethylpyridine derivative of the formula (I) or its salt:

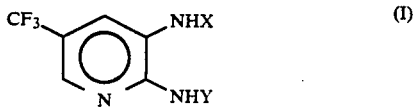

wherein X is $-CW^1R^1$ and Y is $-(NH)_mSO_2R^9$; wherein W is an oxygen or sulfur atom, m is 0 or 1, and $R^1$ and $R^9$ are the same or different and are alkyl, alkenyl, alkenyl, alkynyl, cycloalkyl, cycloalkenyl, phenyl, or a member selected from the group consisting of naphthyl, tetrahydronaphthyl, indanyl, adamantyl, noradamantyl, norbornanyl and norbornanonyl; wherein each of $R^1$ and $R^9$ is optionally substituted with a member selected from the group consisting of a halogen, alkyl, haloalkyl, alkoxy, haloalkoxy, alkylthio, cycloalkyl, cycloalkoxy, cycloalkenyl, cycloalkenyloxy, alkoxycarbonyl, alkylcarbonyl, alkylcarbonyloxy, aryl, aryloxy, arylthio, amino, alkylsubstituted amino, alkylsubstituted cyano and alkylsubstituted nitro.

2. The diaminotrifluoromethylpyridine derivative or its salt according to claim 1, wherein $R^1$ is alkyl, haloalkyl, alkenyl, haloalkenyl, cycloalkyl, halogen-substituted cycloalkyl, phenyl, halogen-substituted phenyl, alkyl- or haloalkyl-substituted phenyl, or alkoxy- or haloalkoxy-substituted phenyl, and $R^9$ is alkyl, haloalkyl, phenyl, halogen-substituted phenyl, alkyl- or haloalkyl-substituted phenyl or alkoxy- or haloalkoxy-substituted phenyl.

3. The diaminotrifluoromethylpyridine derivative or its salt according to claim 1, wherein the diaminotrifluoromethylpyridine derivative is at least one derivative selected from the group consisting of N-(2-ethylsulfonylamino-5-trifluoromethyl-3-pyridyl)cyclohexanecarboxamide, N-(2-methylsulfonylamino-5-trifluoromethyl-3-pyridyl)-5-indanecarboxamide, N-(2-methylsulfonylamino-5-trifluoromethyl-3-pyridyl)acetoxyawcetamide, N-(2-methylsulfonylamino-5-trifluoromethyl-3-pyridyl)crotonamide, N-(2-methylsulfonylamino-5-trifluoromethyl-3-pyridyl)-3-trifluoromethylbenzamide, N-(2-ethylsulfonylamino-5-trifluoromethyl-3-fluorobenzamide, N-(2-methylsulfonylamino-5-trifluoromethyl-3-pyridyl)-6-(1,2,3,4-tetrahydronaphthalene)carboxamide and N-(2-ethylsulfonylamino-5-trifluoromethyl-3-pyridyl)crotonamide.

4. The diaminotrifluoromethylpyridine derivative or its salt according to claim 1, wherein the diaminotrifluoromethylpyridine derivative is N-(2-ethylsulfonylamino-5-trifluoromethyl-3-pyridyl)cyclohexanecarboxamide.

5. A pharmaceutical composition for use as a phospholipase $A_2$ inhibitor, an anti-inflammatory agent or an anti-pancreatic agent which contains as an active ingredient said diaminotrifluoromethylpyridine derivative according to claim 1 and a carrier.

* * * * *

UNITED STATES PATENT AND TRADEMARK OFFICE
CERTIFICATE OF CORRECTION

PATENT NO. : 5,229,403
DATED : July 20, 1993
INVENTOR(S) : Takahiro Haga et al.

It is certified that error appears in the above-indentified patent and that said Letters Patent is hereby corrected as shown below:

On the title page, Item [30],

The second Foreign Application Priority Data has been omitted, please insert: --May 24, 1991  [JP]  Japan........3-222530--

Signed and Sealed this

Twenty-second Day of March, 1994

Attest:

BRUCE LEHMAN

*Attesting Officer*  Commissioner of Patents and Trademarks